(12) United States Patent
Doi et al.

(10) Patent No.: US 8,632,761 B2
(45) Date of Patent: Jan. 21, 2014

(54) HAIR COSMETIC

(75) Inventors: Yasuhiro Doi, Wakayama (JP);
Hiroyuki Terazaki, Wakayama (JP);
Masanori Takai, Wakayama (JP);
Hiromoto Mizushima, Wakayama (JP);
Yoshihiro Hasebe, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/509,082

(22) PCT Filed: Nov. 12, 2010

(86) PCT No.: PCT/JP2010/070211
§ 371 (c)(1),
(2), (4) Date: May 10, 2012

(87) PCT Pub. No.: WO2011/059063
PCT Pub. Date: May 19, 2011

(65) Prior Publication Data
US 2012/0230934 A1 Sep. 13, 2012

(30) Foreign Application Priority Data
Nov. 12, 2009 (JP) .................................. 2009-258955

(51) Int. Cl.
*A61K 8/73* (2006.01)
*A61Q 5/00* (2006.01)
*A61Q 5/02* (2006.01)

(52) U.S. Cl.
USPC .................... 424/70.13; 424/70.1; 424/70.22; 514/880; 514/881

(58) Field of Classification Search
USPC .................................. 424/70.1, 70.13, 70.22
See application file for complete search history.

(56) References Cited

U.S. PATENT DOCUMENTS

| 3,472,840 A | 10/1969 | Stone et al. |
| 3,816,616 A | 6/1974 | Anguillo et al. |
| 2006/0073110 A1 | 4/2006 | Modi |
| 2010/0274001 A1 | 10/2010 | Okutsu et al. |

FOREIGN PATENT DOCUMENTS

| EP | 0 149 249 | 7/1985 |
| JP | 45 20318 | 7/1970 |
| JP | 54 87787 | 7/1979 |
| JP | 59 42681 | 10/1984 |
| JP | 4 230614 | 8/1992 |
| JP | 2000 143462 | 5/2000 |
| JP | 2000327541 A | * 11/2000 |
| JP | 2009 143997 | 7/2009 |

OTHER PUBLICATIONS

International Search Report Issued Jan. 11, 2011 in PCT/JP10/70211 Filed Nov. 12, 2010.

* cited by examiner

*Primary Examiner* — Lezah Roberts
*Assistant Examiner* — Tracy Liu
(74) *Attorney, Agent, or Firm* — Oblon, Spivak, McClelland, Maier & Neustadt, L.L.P.

(57) ABSTRACT

The present invention relates to a hair cosmetic composition including a surfactant and a cationized hydroxypropyl cellulose, wherein the cationized hydroxypropyl cellulose contains a main chain derived from an anhydroglucose represented by the following general formula (1) and has a cationized ethyleneoxy group substitution degree of from 0.01 to 2.5 and a propyleneoxy group substitution degree of from 0.1 to 2.8,

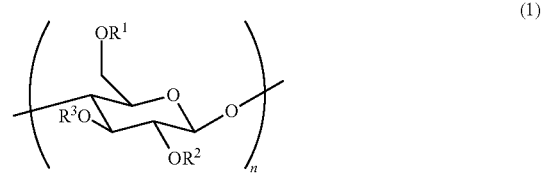

(1)

wherein $R^1$, $R^2$ and $R^3$ are each independently a substituent group including a cationized ethyleneoxy group and a propyleneoxy group; and n represents an average polymerization degree of the anhydroglucose and is a number of from 50 to 5000. The hair cosmetic composition of the present invention exhibits a less stickiness after use and is capable of imparting excellent run fingers through hair, coating feel and manageability to hair.

22 Claims, No Drawings

HAIR COSMETIC

CROSS REFERENCE TO RELATED APPLICATION

This application is a 371 of PCT/JP2010/070211, filed on Nov. 12, 2010, and claims priority to Japanese Patent Application No. 2009-258955, filed on Nov. 12, 2009.

FIELD OF THE INVENTION

The present invention relates to hair cosmetic compositions containing cationized hydroxypropyl celluloses.

BACKGROUND OF THE INVENTION

Hairs are damaged by living environments (such as ultraviolet radiation and heat due to sunlight, and drying), daily hair care behaviors (such as washing, brushing and drying by heat using a dryer) or chemical treatments (such as coloring and permanent waving). For this reason, in order to coat a surface of hair and restore smooth feeling thereof, various measures have been taken for improving hair cosmetic compositions.

For example, for the purpose of improving run fingers through hair, softness, manageability and coating feel, conditioning agents as the hair cosmetic compositions are generally compounded with a cationic polymer or an oil such as silicones, ester oils and mineral oils. However, if the amount of these components compounded in the conditioning agents is increased to attain an enhanced compounding effect, the hair treated therewith tends to suffer from sticky or greasy feel after drying which leads to poor feeling upon use. On the other hand, if the amount of the components compounded is reduced in order to suppress the stickiness of hair, the resulting conditioning agents tend to be insufficient in conditioning effect. In addition, if hair shampoos are compounded with a large amount of the conditioning agents, the hair shampoos tend to be deteriorated in a foaming property as well as feeling upon use when shampooing.

JP 60-170601A discloses a novel polysaccharide which is capable of imparting desirable properties to personal care products such as hair care compositions.

JP 4-230614A discloses a hair cosmetic composition which contains an alkyl polyalkylene glycol ether, a cationic surfactant and a fatty acid having 12 to 40 carbon atoms at specific proportions to improve sticky feel and greasy feel and impart good touch feel to damaged hair.

JP 2000-143462A discloses a hair cosmetic composition having a less sticky feel after drying and an excellent smooth feel in which a specific synthetic cationic polymer is used in combination with a surfactant.

JP 2008-514604A discloses a skin care composition which aims at attaining a skin protecting effect and is constituted from a surfactant, a specific cationic polymer and a skin care active component, and further may contain various additives such as functional polymers, if required. In JP 2008-514604A, as an example of a number of the functional polymers, there are mentioned cationic hydroxypropyl celluloses (refer to paragraphs [0025] to [0026] of JP 2008-514604A).

However, the hair cosmetic compositions described in the above patent documents have failed to attain a level capable of fully satisfying various properties including excellent feeling upon use such as good run fingers through hair, less stickiness and good coating feel of hair after drying.

SUMMARY OF THE INVENTION

The present invention relates to a hair cosmetic composition including a surfactant and a cationized hydroxypropyl cellulose, wherein the cationized hydroxypropyl cellulose contains a main chain derived from an anhydroglucose represented by the following general formula (1) and has a cationized ethyleneoxy group substitution degree of from 0.01 to 2.5 and a propyleneoxy group substitution degree of from 0.1 to 2.8.

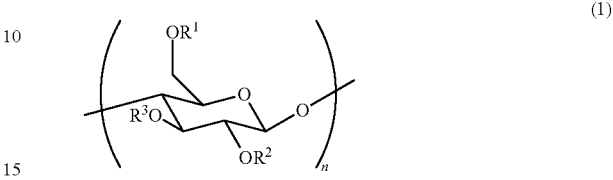

wherein $R^1$, $R^2$ and $R^3$ are each independently a substituent group including a cationized ethyleneoxy group and a propyleneoxy group; and n represents an average polymerization degree of the anhydroglucose and is a number of from 50 to 5000.

DETAILED DESCRIPTION OF THE INVENTION

The present invention relates to a hair cosmetic composition which exhibits a less stickiness after use and is capable of imparting excellent run fingers through hair, coating feel and manageability to hair.

The present inventors have found that the above problems can be solved by incorporating a specific cationized hydroxypropyl cellulose to a hair cosmetic composition.

That is, the present invention relates to a hair cosmetic composition including a surfactant and a cationized hydroxypropyl cellulose, wherein the cationized hydroxypropyl cellulose contains a main chain derived from an anhydroglucose represented by the following general formula (1) and has a cationized ethyleneoxy group substitution degree of from 0.01 to 2.5 and a propyleneoxy group substitution degree of from 0.1 to 2.8.

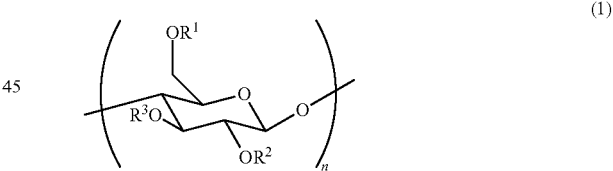

wherein $R^1$, $R^2$ and $R^3$ are each independently a substituent group represented by the following general formula (2) including a cationized ethyleneoxy group and a propyleneoxy group; and n represents an average polymerization degree of the anhydroglucose and is a number of from 50 to 5000.

$R^1$, $R^2$, $R^3$:

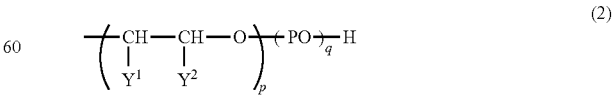

wherein one of $Y^1$ and $Y^2$ is a hydrogen atom and the other of $Y^1$ and $Y^2$ is a cationic group represented by the following general formula (3); PO is a propyleneoxy group; and p represents a number of cationized ethyleneoxy groups (—CH ($Y^1$)—CH($Y^2$)—O—) contained in the general formula (2) and q is a number of propyleneoxy groups (—PO—) contained in the general formula (2), and p and q are respectively 0 or a positive number with the proviso that when neither p nor q is 0, the order of addition of the cationized ethyleneoxy group and the propyleneoxy group is not limited, and when neither p nor q is 0 and p and/or q are 2 or more, the cationized ethyleneoxy group and the propyleneoxy group may be added by a block bond or a random bond.

$Y^1, Y^2$:

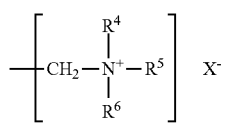

(3)

wherein $R^4$, $R^5$ and $R^6$ are each independently a linear or branched alkyl group having 1 to 3 carbon atoms; and $X^-$ is an anionic group.

From the viewpoints of enhancement in run fingers through hair, coating feel and manageability and reduction in stickiness of hair treated with the hair cosmetic composition after drying, the cationized ethyleneoxy group substitution degree of the cationized hydroxypropyl cellulose contained in the hair cosmetic composition is 0.01 or more, preferably 0.02 or more, more preferably 0.03 or more, still more preferably 0.06 or more, and especially preferably 0.08 or more. Also, from the viewpoint of a good manageability after drying the hair treated with the hair cosmetic composition, the cationized ethyleneoxy group substitution degree is 2.5 or less, preferably 2.0 or less, more preferably 1.5 or less, still more preferably 0.8 or less, and especially preferably 0.6 or less. From these total viewpoints, the cationized ethyleneoxy group substitution degree of the cationized hydroxypropyl cellulose is from 0.01 to 2.5, preferably from 0.01 to 2.0, more preferably from 0.02 to 1.5, still more preferably from 0.03 to 0.8, further still more preferably from 0.06 to 0.8, and especially preferably from 0.08 to 0.6.

In the present invention, the cationized ethyleneoxide group substitution degree as used herein means an average molar number of a cationized ethyleneoxy group being present in a molecule of the cationized hydroxypropyl cellulose (hereinafter occasionally referred to merely as "C-HPC") per 1 mol of an anhydroglucose unit constituting a main chain of the cellulose. The cationized ethyleneoxide group substitution degree may be measured by the method described in Examples below.

The cationized hydroxypropyl cellulose used in the present invention means a compound having such a structure as represented by the above general formula (1). Upon production of the cationized hydroxypropyl cellulose, the order of cationization and hydroxypropylation of the cellulose may be optional, and any of the cationization and hydroxypropylation may be first conducted, or the cationization and hydroxypropylation may be conducted at the same time.

From the viewpoints of enhancement in run fingers through hair, coating feel and manageability and reduction in sticky or greasy feel of hair treated with the hair cosmetic composition after drying, the cationized hydroxypropyl cellulose has a propyleneoxy group substitution degree of 0.1 or more, preferably 0.2 or more, more preferably 0.5 or more, and still more preferably 0.8 or more. Also, from the viewpoints of enhancement in run fingers through hair, coating feel and manageability and reduction in sticky or greasy feel of hair treated with the hair cosmetic composition after drying, the cationized hydroxypropyl cellulose has a propyleneoxy group substitution degree of 2.8 or less, preferably 2.6 or less, more preferably 2.4 or less, and still more preferably 2.3 or less.

The "propyleneoxy group substitution degree" as used in the present invention means an average molar number of a propyleneoxy group being present in a molecule of the C-HPC per 1 mol of an anhydroglucose unit constituting a main chain of the cellulose. The propyleneoxy group substitution degree may be measured by the method described in Examples below.

From the viewpoint of easiness of production of the cationized hydroxypropyl cellulose, a sum of the cationized ethyleneoxy group substitution degree and the propyleneoxy group substitution degree is preferably 3.0 or less. From the viewpoints of enhancement in run fingers through hair, coating feel and manageability of hair treated with the hair cosmetic composition after drying, the sum of the cationized ethyleneoxy group substitution degree and the propyleneoxy group substitution degree is preferably 0.9 or more.

From the viewpoints of attaining excellent run fingers through hair, coating feel and manageability of hair treated with the hair cosmetic composition after drying, the average polymerization degree (n) of an anhydroglucose in the cationized hydroxypropyl cellulose is from 50 to 5000, preferably from 100 to 2000, more preferably from 300 to 1500, and still more preferably from 350 to 1350.

Meanwhile, the "average polymerization degree" as used in the present invention means a viscosity-average polymerization degree which may be measured by a copper-ammonia method, more specifically, may be measured by the method described in Examples below.

(Substituent Group Represented by the General Formula (2))

The substituent group represented by the general formula (2) includes a cationized ethyleneoxy group and a propyleneoxy group as shown in the following formula (2).

$R^1, R^2, R^3$:

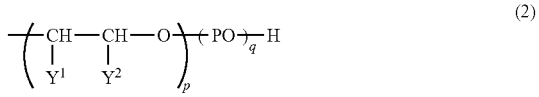

(2)

In the above general formula (2), one of $Y^1$ and $Y^2$ is a hydrogen atom and the other of $Y^1$ and $Y^2$ is a cationic group represented by the following general formula (3); and PO is a propyleneoxy group.

The suffix p represents a number of cationized ethyleneoxy groups (—CH($Y^1$)—CH($Y^2$)—O—) contained in the general formula (2), and the suffix q represents a number of propyleneoxy groups (—PO—) contained in the general formula (2), and p and q are respectively 0 or a positive number.

The suffixes p and q are respectively preferably 0 or 1 from the viewpoint of easiness of production of the cationized hydroxypropyl cellulose. When neither p nor q is 0, the order of addition of the cationized ethyleneoxy group and the propyleneoxy group is not limited. However, from the viewpoint of easiness of production of the cationized hydroxypropyl cellulose, the order of addition of these groups is preferably as shown in the above formula (2). In addition, when neither p nor q is 0 and p and/or q are 2 or more, the cationized ethyleneoxy group and the propyleneoxy group may be added by a block bond or a random bond. However, from the viewpoint of easiness of production of the cationized hydroxypropyl cellulose, among these bonds, preferred is a block bond.
(Cationic Group Represented by the General Formula (3))

The cationic group represented by the general formula (3) has a structure represented by the following formula (3).

$Y^1, Y^2$:

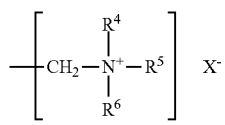

(3)

In the above general formula (3), $R^4$, $R^5$ and $R^6$ are each independently a linear or branched alkyl group having 1 to 3 carbon atoms. Specific examples of the linear or branched alkyl group include a methyl group, an ethyl group, an n-propyl group and an isopropyl group. Among these alkyl groups, from the viewpoint of a good water solubility of the C-HPC, preferred are a methyl group and an ethyl group, and especially preferred is a methyl group.

In the general formula (3), $X^-$ is an anionic group as a counter ion of an ammonium salt. $X^-$ is not particularly limited as long as it is an anionic group. Specific examples of the anionic group as $X^-$ include an alkylsulfuric acid ion, a sulfuric acid ion, a phosphoric acid ion, an alkyl-carboxylate ion, and a halogen ion. Among these anionic groups, from the viewpoint of easiness of production of the cationized hydroxypropyl cellulose, preferred is a halogen ion. Examples of the halogen ion include a fluorine ion, a chlorine ion, a bromine ion and an iodine ion. Among these halogen ions, from the viewpoints of a good water solubility and a high chemical stability of the C-HPC, preferred are a chlorine ion and a bromine ion, and especially preferred is a chlorine ion.

[Production of Cationized Hydroxypropyl Cellulose (C-HPC)]

The C-HPC may be produced, for example, by the following production methods (1) to (3).

(1) Method of mixing a cellulose with a large amount of water and an excessively large amount of an alkali metal hydroxide to form a slurry, and then reacting the resulting slurry with a cationizing agent and propyleneoxide.

(2) Method of dissolving a cellulose using dimethyl acetamide containing lithium chloride as a solvent by further adding an amine or an alcoholate catalyst thereto, and then reacting the resulting solution with a cationizing agent and propyleneoxide.

(3) Method of reacting a cellulose in the form of a powder, pellets or chips with a cationizing agent and propyleneoxide in the presence of a base without using an excessive amount of water or a solvent as in the above methods (1) and (2).

In the above production methods (1) to (3), any of the reaction with the cationizing agent and the reaction with propyleneoxide may be first conducted, or both the reactions may be conducted at the same time.

Among the above production methods, from the viewpoint of easiness of production of the cationized hydroxypropyl cellulose, preferred is the production method (3).

The production method (3) preferably includes the following steps (1) and (2).

Step (1): adding a cationizing agent to a pulp and subjecting the resulting mixture to mill treatment to reduce a crystallinity of the pulp, and then adding a base to the obtained mixture and subjecting the mixture to mill treatment to react the pulp with the cationizing agent while further reducing a crystallinity of the pulp, thereby obtaining a cationized cellulose; and Step (2): reacting the cationized cellulose obtained in the step (1) with propyleneoxide to obtain a cationized hydroxypropyl cellulose.

In the following, the above production method (3) is more specifically explained.

(Raw Cellulose)

In the cellulose used for production of the C-HPC, a crystalline moiety thereof generally has a low reactivity. Therefore, as the raw cellulose, there may be suitably used (i) a low-crystalline powdery cellulose which is obtained by reducing a crystallinity of the cellulose, or (ii) a high-crystalline pulp.

<Production of C-HPC Using the Low-Crystalline Powdery Cellulose (i)>

The low-crystalline powdery cellulose used in the present invention may be produced from sheet-like or roll-like pulps having a high cellulose purity as generally available raw materials. The method for producing the low-crystalline powdery cellulose is not particularly limited, and the low-crystalline powdery cellulose may be produced, for example, by the production methods described in JP 62-236801A, JP 2003-64184A and JP 2004-331918A, etc. Among these celluloses, preferred are low-crystalline or non-crystalline powdery celluloses obtained by subjecting the raw materials to mechanochemical treatment (hereinafter generally referred to as a "low-crystalline powdery cellulose").

The term "low-crystalline" of the low-crystalline powdery cellulose as used herein means the condition in which the proportion of an amorphous moiety in a crystal structure of the cellulose is large, and more specifically means that the crystallinity of the powdery cellulose as calculated from the following calculation formula (1) is preferably 30% or less, more preferably 20% or less and still more preferably 10% or less. In particular, in the present invention, completely amorphized celluloses having a crystallinity of substantially 0% are most preferably used.

$$\text{Crystallinity (\%)}=[(I_{22.6}-I_{18.5}/I_{22.6}]\times 100 \tag{1}$$

wherein $I_{22.6}$ is a diffraction intensity of a lattice plane (002 plane) as measured at a diffraction angle $2\theta$ of $22.6°$ in X-ray diffraction analysis; and $I_{18.5}$ is a diffraction intensity of an amorphous moiety as measured at a diffraction angle $2\theta$ of $18.5°$ in X-ray diffraction analysis.

As the method for producing the low-crystalline powdery cellulose by the mechanochemical treatment, there may be mentioned the method of treating chip-like pulps obtained, for example, by coarsely milling sheet-like pulps, using a mill. The chip-like pulps may be treated by an extruder before the treatment using the mill.

The extruder used in the above production method may be either a single-screw extruder or a twin-screw extruder. Among these extruders, preferred is a twin-screw extruder. From the viewpoint of applying a strong compression shear force to the pulps, there is preferably used the twin-screw extruder which may be equipped with so-called kneading disks in any portion of screws thereof.

The method of treating the pulps by the extruder is not particularly limited. The chip-like pulps are preferably continuously charged into the extruder and treated therein.

Examples of the mill which may be used in the above production method include roll mills such as a high-pressure compression roll mill and a roll rotating mill, vertical roller mills such as a ring roller mill, a roller race mill and a ball race mill, container-driving media mills such as a rolling ball mill, a vibration ball mill, a vibration rod mill, a vibration tube mill, a planetary ball mill and a centrifugal fluidization mill, media-stirring mills such as a tower mill, an agitation tank mill, a flowing tank mill and an annular mill, compaction shearing mills such as a high-speed centrifugal roller mill and an ang mill, mortars, and stone grist mills. Among these mills, from the viewpoints of a high efficiency of reducing a crystallinity of the cellulose and a high productivity, preferred are container-driving media mills and media-stirring mills, more preferred are container-driving media mills, still more preferred are vibration mills such as a vibration ball mill, a vibration rod mill and a vibration tube mill, and especially preferred are a vibration ball mill and a vibration rod mill.

The treatment using the mills may be conducted by either a batch method or a continuous method.

The suitable filling percentage of the milling medium such as balls and rods in the mills may vary depending upon the kinds of mills used, and is preferably in the range of from 10 to 97%, and more preferably from 15 to 95%. When the filling percentage of the milling medium is present within the above-specified range, it is possible to enhance a frequency of contact between the raw pulps and the milling medium and improve a milling efficiency without inhibiting movement of the milling medium. Meanwhile, the "filling percentage" as used herein means a ratio of an apparent volume of the milling medium to a capacity of a stirring portion of the mill.

The material of the balls used as the milling medium in the ball mills is not particularly limited. Examples of the material of the balls include iron, stainless steel, alumina and zirconia. The outer diameter of the balls is preferably from 0.1 to 100 mm, and more preferably from 1 to 50 mm from the viewpoint of efficiently reducing a crystallinity of the cellulose.

The mill treatment time of the cellulose is preferably from 5 min to 72 h and more preferably from 10 min to 30 h to efficiently reduce a crystallinity of the cellulose. The mill treatment is preferably carried out at a temperature of 250° C. or lower, and more preferably from 5 to 200° C. to minimize degradation or deterioration of the cellulose due to heat generated upon the mill treatment.

The "rod" used as the milling medium in the mills means a bar-shaped milling medium, and has a shape in section including a polygonal shape such as a quadrangular shape and a hexagonal shape, a circular shape and an ellipsoidal shape.

The outer diameter of the rod is preferably in the range of from 0.5 to 200 mm, more preferably from 1 to 100 mm and still more preferably from 5 to 50 mm. The length of the rod is not particularly limited as long as the rod has a length shorter than that of a container of the mill. When the rod has the above specified size, it is possible to attain a desired milling force and thereby efficiently reduce a crystallinity of the cellulose.

The treating time and treating temperature of the vibration mill filled with the rods are not particularly limited, and may be similar to those used above for the ball mills.

According to the above production method, it is possible to control a molecular weight of the cellulose and, therefore, produce a powdery cellulose having a high polymerization degree and a low crystallinity which tends to be hardly generally available. The average polymerization degree of the low-crystalline powdery cellulose is preferably from 100 to 2000, more preferably from 300 to 1500 and still more preferably from 350 to 1350.

The average particle size of the low-crystalline powdery cellulose is not particularly limited as long as a good fluidity of the powdery cellulose can be ensured, and is preferably 300 μm or less, more preferably 150 μm or less and still more preferably 50 μm or less. Meanwhile, from the viewpoint of easiness of handling of the powdery cellulose, the average particle size of the low-crystalline powdery cellulose is preferably 20 μm or more, and more preferably 25 μm or more. However, in order to avoid inclusion of a trace amount of coarse particles owing to aggregation, etc., it is desirable that undersize particles obtained by passing the powdery cellulose through a sieve having a mesh size of from about 300 to about 1000 μm are used in the reaction, if required.

(Cationization of Low-Crystalline Powdery Cellulose)

The thus obtained low-crystalline powdery cellulose is then cationized by reacting with a glycidyl trialkyl ammonium salt in the presence of a base to thereby produce a cationized cellulose.

Examples of the glycidyl trialkyl ammonium salt used as a cationizing agent include glycidyl trimethyl ammonium chloride, glycidyl triethyl ammonium chloride, glycidyl trimethyl ammonium bromide and glycidyl triethyl ammonium bromide. Among these glycidyl trialkyl ammonium salts, glycidyl trimethyl ammonium chloride is preferred from the viewpoint of a good availability. The amount of the glycidyl trialkyl ammonium salt added is usually from 0.01 to 3.0 mol, preferably from 0.02 to 2 mol and more preferably from 0.04 to 1.0 mol per 1 mol of an anhydroglucose unit contained in the cellulose from the viewpoints of enhancement in run fingers through hair, coating feel and manageability and reduction in sticky or greasy feel of hair treated with the hair cosmetic composition after drying.

Examples of the base to be present upon the cationization include lithium hydroxide, sodium hydroxide, potassium hydroxide, calcium hydroxide and barium hydroxide. From the viewpoints of good availability, flexibility and economy, among these bases, preferred are sodium hydroxide and barium hydroxide. The amount of the base added may vary depending upon the kind of cellulose used, and is usually from 0.05 to 1.0 mol, preferably from 0.1 to 0.5 mol and more preferably from 0.2 to 0.3 mol per 1 mol of an anhydroglucose unit contained in the cellulose.

The water content in the reaction system upon the above cationization reaction is preferably 100% by mass or less on the basis of the cellulose used as the raw material. When the water content based on the cellulose lies within the above-specified range, it is possible to react the cellulose in a fluidizable powdery state without occurrence of excessive aggregation thereof. From this viewpoint, the water content in the reaction system upon the cationization reaction is more preferably 80% by mass or less and still more preferably from 5 to 50% by mass.

The reaction temperature used upon the cationization reaction is usually from 10 to 85° C. and preferably from 15 to 80° C.

(Hydroxypropylation of Cationized Cellulose)

The cationized cellulose thus obtained above is then reacted with propyleneoxide for hydroxypropylation thereof to thereby produce the C-HPC.

The amount of the propyleneoxide used upon the hydroxypropylation reaction is in the range of from 0.01 to 5.0 mol, preferably from 0.1 to 3.0 mol and more preferably from 0.5 to 2.5 mol per 1 mol of an anhydroglucose unit contained in a molecule of the cellulose from the viewpoints of enhancement in run fingers through hair, coating feel and manageability and reduction in sticky or greasy feel of hair treated with the hair cosmetic composition after drying.

The catalyst used in the hydroxypropylation reaction may be either a base catalyst or an acid catalyst. Examples of the base catalyst include alkali metal hydroxides such as sodium hydroxide, potassium hydroxide and lithium hydroxide, alkali earth metal hydroxides such as magnesium hydroxide and calcium hydroxide, and tertiary amines such as trimethylamine, triethylamine and triethylene diamine. Examples of the acid catalyst include Lewis acid catalysts such as lanthanide triflates.

Among these catalysts, from the viewpoint of suppressing deterioration in polymerization degree of the raw cellulose, preferred are base catalysts, more preferred are alkali metal hydroxides, and still more preferred are sodium hydroxide and potassium hydroxide. These catalysts may be used alone or in combination of any two or more thereof.

The amount of the catalyst used in the hydroxypropylation reaction is not particularly limited, and the catalyst is usually used in an amount of from 0.05 to 1.0 mol, preferably from 0.1 to 0.8 mol and more preferably from 0.2 to 0.5 mol per 1 mol of an anhydroglucose unit contained in a molecule of the cellulose.

The method of adding the propyleneoxide is not particularly limited, and there may be used, for example, (c) the method of adding the catalyst to the cationized cellulose and then dropping the propyleneoxide to the resulting mixture, (d) the method of adding the propyleneoxide to the cationized cellulose at one time and then gradually adding the catalyst to the resulting mixture to conduct a reaction therebetween, etc. Among these methods, preferred is the method (c).

The water content in the reaction system upon the above hydroxypropylation reaction is preferably 100% by mass or less on the basis of the cellulose used as the raw material. When the water content based on the cellulose lies within the above-specified range, it is possible to react the cationized cellulose in a fluidizable powdery state without occurrence of excessive aggregation thereof. From this viewpoint, the water content in the reaction system upon the hydroxypropylation reaction is more preferably 80% by mass or less and still more preferably from 5 to 50% by mass.

In the present invention, the cationized cellulose, the catalyst and the propyleneoxide are preferably reacted with each other in a fluidizable powdery state. However, there may also be used the method in which the cationized cellulose and the catalyst are previously mixed with each other using a mixing device such as a mixer or a shaker, or a mixing mill, if required to uniformly mix and disperse these components, and then adding the propyleneoxide to the resulting mixture to react therewith.

The reaction temperature used upon the hydroxypropylation reaction is preferably from 0 to 150° C. From the viewpoint of avoiding occurrence of polymerization between molecules of the propyleneoxide and rapid proceeding of the reaction, the hydroxypropylation reaction temperature is more preferably from 10 to 100° C. and still more preferably from 20 to 80° C. The hydroxypropylation reaction may be carried out under normal pressures.

Also, from the viewpoints of avoiding decrease in molecular weight of the cellulose owing to cleavage of cellulose chains during the reaction, it is preferable to conduct the reaction in an inert gas atmosphere such as nitrogen.

After completion of the reaction, unreacted propyleneoxide is removed from the reaction product, and then the resulting product is subjected to neutralization treatment, purification treatment, etc., if required, and then dried, thereby obtaining the C-HPC according to the present invention.

The neutralization treatment may be carried out by an ordinary method. For example, when using the base catalyst, the neutralization treatment may be carried out by adding an acid solution such as acetic acid, a mixed solution of an acid and an inert organic solvent or an acid aqueous solution to the reaction product. The acid used for the neutralization treatment is not particularly limited, and may be appropriately selected in view of corrosion of an apparatus used therefor, etc. The purification treatment may be carried out by washing with a solvent such as hydrous isopropanol or hydrous acetone and/or water, or using a dialysis membrane.

In the production of the C-HPC using the above low-crystalline powdery cellulose (i), the order of the cationization reaction and the hydroxypropylation reaction may be optional, i.e., the cationization reaction may be carried out after subjecting the raw cellulose to the hydroxypropylation reaction, or the cationization reaction and the hydroxypropylation reaction may be carried out at the same time. From the viewpoint of well controlling the cationized ethyleneoxy group substitution degree and the propyleneoxy group substitution degree, it is preferred that after cationizing the raw cellulose, the resulting cationized cellulose is subjected to hydroxypropylation reaction.

In the cationization reaction and the hydroxypropylation reaction upon production of the C-HPC using the low-crystalline powdery cellulose (i), there occurs substantially no cleavage of the cellulose skeleton as a main chain thereof. Therefore, the average polymerization degree of the resulting C-HPC may approximate to an average polymerization degree of the powdery cellulose after subjected to the crystallinity-reducing treatment.

<Production of C-HPC Using High-Crystalline Pulp (ii)>
(Cationization of Pulp)

In the case where the high-crystalline pulp is used as the raw cellulose in place of the above low-crystalline powdery cellulose, the pulp is preferably subjected to crystallinity-reducing treatment upon the cationization reaction in order to improve a reactivity of the pulp.

More specifically, the cationizing agent is added to the pulp, and the resulting mixture is subjected to mill treatment to reduce a crystallinity of the pulp, and then the base is added to the milled product, and the resulting mixture is further subjected to mill treatment to conduct the reaction between the pulp and the cationizing agent while reducing a crystallinity of the pulp to thereby produce the cationized cellulose. Alternatively, the base is added to the pulp, and the resulting mixture is subjected to mill treatment to reduce a crystallinity of the pulp, and then the cationizing agent is added to the milled product, and the resulting mixture is further subjected to mill treatment to conduct the reaction between the pulp and the cationizing agent while reducing a crystallinity of the pulp to thereby produce the cationized cellulose.

From the viewpoints of a good dissolvability in water of the C-HPC produced through the cationization reaction, the cellulose is preferably cationized by the method in which the cationizing agent is first added to the pulp, and the resulting mixture is subjected to mill treatment to reduce a crystallinity of the pulp, and then the base is added to the milled product, and the resulting mixture is further subjected to mill treatment to conduct the reaction between the pulp and the cationizing agent while reducing a crystallinity of the pulp.

The shape of the pulp used as the raw cellulose is not particularly limited, and there may be used pulps having various shapes as long as they can be introduced into the production apparatus without any difficulty or problems. From the viewpoint of a good operation, sheet-like pulps, or pellet-like or chip-like pulps obtained by cutting or coarsely crushing the sheet-like pulps, or powdery celluloses obtained by finely milling the pulps are preferably used.

The crystallinity of the pulps used as the raw cellulose is not particularly limited. However, the treatment for reducing a crystallinity of the pulps tends to generally cause reduction in molecular weight thereof owing to cutting of cellulose chains. Therefore, in order to produce a cationized cellulose having a higher molecular weight, it is preferred to use the raw cellulose which undergoes less decrease in molecular weight and has a higher crystallinity, as the raw cellulose. On the contrary, it is also difficult to obtain the raw cellulose having an extremely high crystallinity exceeding 95% as calculated from the above formula (1). For this reason, from the viewpoint of a high polymerization degree and a good availability, the crystallinity of the pulps used as the raw cellulose as calculated from the above formula (1) is preferably from 10 to 95%, more preferably from 30 to 90% and still more preferably from 60 to 80%.

The average polymerization degree of the raw cellulose is also not particularly limited. However, in order to obtain a cationized cellulose having a higher molecular weight, it is preferred to use the raw cellulose having a higher polymerization degree. From this viewpoint, the average polymerization degree of the raw cellulose is preferably from 100 to 2000, more preferably from 300 to 1500 and still more preferably from 350 to 1350.

The preferred conditions of kind and amount of cationizing agent, kind of base, kind of mill and method and conditions for reducing a crystallinity of the raw cellulose, etc., which are used for the production of C-HPC using the high-crystallinity pulp (ii) are the same as those described with respect to the above production of C-HPC using the low-crystalline powdery cellulose (i) except for the treating time of the mill treatment for reducing a crystallinity of the pulp. The treating time of the mill treatment for reducing a crystallinity of the pulp is preferably from 1 min to 5 h, more preferably from 2 min to 3 h and still more preferably from 5 min to 2 h. When the base is used in an amount of 0.01 equivalent or more per 1 mol of an anhydroglucose unit in the raw cellulose, the reaction between the cellulose and the cationizing agent is allowed to proceed rapidly. Whereas, when the base is used in an amount of 1 equivalent or less per 1 mol of an anhydroglucose unit in the raw cellulose, the reaction between the cellulose and the cationizing agent is carried out with a high yield. From these viewpoints, the amount of the based used per 1 mol of an anhydroglucose unit in the raw cellulose is preferably from 0.05 to 0.8 equivalent, more preferably from 0.1 to 0.7 equivalent, still more preferably from 0.2 to 0.6 equivalent, and especially preferably from 0.3 to 0.5 equivalent.

The cationization reaction is caused to proceed upon the crystallinity-reducing treatment after adding the cationizing agent and the base. However, if the cationization reaction fails to proceed sufficiently, the aging treatment is preferably carried out at a temperature of from 10 to 100° C. and more preferably from 30 to 80° C. to thereby allow the reaction to proceed.

The water content and preferred conditions upon the aging treatment are the same as those used in the above cationization of the low-crystalline powder cellulose except for using the pulps as the raw material in place of the low-crystalline powder cellulose.

From the viewpoint of avoiding reduction in molecular weight owing to cleavage of cellulose chains during the reaction, the aging treatment is preferably carried out in an inert gas atmosphere such as nitrogen.

(Hydroxypropylation of Cationized Cellulose)

The amount of propyleneoxide, catalyst, reaction conditions, treatments after completion of the reaction, and preferred conditions thereof which are used for hydroxypropylation of the cationized cellulose upon the production of C-HPC using the high-crystallinity pulp (ii), are the same as those used for hydroxypropylation upon the above production of C-HPC using the low-crystalline powdery cellulose (i).

In the present invention, among the above-described production methods of C-HPC, from the viewpoints of attaining excellent run fingers through hair and coating feel of hair treated with the hair cosmetic composition according to the present invention after drying, preferred is the production method mentioned with respect to the production of C-HPC using the high-crystallinity pulp (ii) in which the crystallinity-reducing treatment is carried out upon the cationization reaction, and the resulting cationized cellulose is subjected to hydroxypropylation reaction.

From the viewpoints of enhancement in run fingers through hair, coating feel and manageability and reduction in sticky or greasy feel of hair treated with the hair cosmetic composition after drying, the cationized ethyleneoxy group substitution degree in a molecule of the C-HPC is from 0.01 to 2.5 as described above, preferably from 0.01 to 2.0, more preferably from 0.02 to 1.5, still more preferably from 0.03 to 0.8, further still more preferably from 0.06 to 0.8 and especially preferably from 0.08 to 0.6. The propyleneoxy group substitution degree in a molecule of the C-HPC is from 0.1 to 2.8, preferably from 0.2 to 2.6, more preferably from 0.5 to 2.4 and still more preferably from 0.8 to 2.3 from the viewpoints of enhancement in run fingers through hair, coating feel and manageability and reduction in sticky or greasy feel of hair treated with the hair cosmetic composition after drying.

(Hair Cosmetic Composition and Production Process Thereof)

The hair cosmetic composition according to the present invention contains the C-HPC and a surfactant.

The production process of the hair cosmetic composition is not particularly limited. However, in the production process including the following steps (1) to (3) according to the present invention, it is possible to efficiently produce the hair cosmetic composition which is capable of imparting excellent run fingers through hair, coating feel and manageability to hair without sticky or greasy feel after use.

Step (1): adding a cationizing agent to a pulp and subjecting the resulting mixture to mill treatment to reduce a crystallinity of the pulp, and then adding a base to the obtained mixture and subjecting the mixture to mill treatment to react the pulp with the cationizing agent while further reducing a crystallinity of the pulp, thereby obtaining a cationized cellulose;

Step (2); reacting the cationized cellulose obtained in the step (1) with propyleneoxide to obtain a cationized hydroxypropyl cellulose; and Step (3): mixing the cationized hydroxypropyl cellulose obtained in the step (2) with a surfactant.

The details of the steps (1) and (2) are the same as described above. The step (3) is a step in which the cationized hydroxypropyl cellulose obtained in the step (2) is mixed with a surfactant. The mixing method is not particularly limited.

In the following, the contents of the C-HPC and the surfactant in the hair cosmetic composition are described.

The content of the C-HPC in the hair cosmetic composition is preferably 0.005% by mass or more, more preferably 0.02% by mass or more, still more preferably 0.03% by mass or more, further still more preferably 0.04% by mass or more, and especially preferably 0.05% by mass or more from the viewpoints of attaining excellent run fingers through hair, coating feel and manageability of hair treated with the hair cosmetic composition after drying. On the other hand, from the viewpoints of suppressing sticky or greasy feel of hair treated with the hair cosmetic composition after drying, the content of the C-HPC in the hair cosmetic composition is preferably 10% by mass or less, more preferably 5% by mass or less, still more preferably 2% by mass or less, further still more preferably 1% by mass or less, and especially preferably 0.5% by mass or less. From these total viewpoints, the content of the C-HPC in the hair cosmetic composition is preferably from 0.005 to 10% by mass, more preferably from 0.02 to 5% by mass, still more preferably from 0.03 to 2% by mass, further still more preferably from 0.04 to 1% by mass, and especially preferably from 0.05 to 0.5% by mass.

The hair cosmetic composition further contains a surfactant.

Examples of the surfactant include an anionic surfactant, a nonionic surfactant, a cationic surfactant and an amphoteric surfactant.

When the hair cosmetic composition according to the present invention is used as a cleansing agent such as a shampoo, among the above surfactants, preferred are the anionic surfactant, the nonionic surfactant and the amphoteric surfactant. On the other hand, when the hair cosmetic composition according to the present invention is used as a rinse, a conditioner, a treatment, a hair styling agent, etc., among the above surfactants, preferred are the nonionic surfactant and the cationic surfactant.

Examples of the anionic surfactant include a sulfuric acid ester salt, a sulfonic acid salt, a carboxylic acid salt, a phosphoric acid ester salt and an amino acid salt. Specific examples of the sulfuric acid ester salt include alkyl sulfuric acid salts, polyoxyalkylene alkyl ether sulfuric acid salts, polyoxyalkylene alkenyl ether sulfuric acid salts and polyoxyalkylene alkyl phenyl ether sulfuric acid salts. Specific examples of the sulfonic acid salt include sulfosuccinic alkyl ester salts, polyoxyalkylene sulfosuccinic alkyl ester salts, alkane sulfonic acid salts, acyl isethionate and acyl methyl taurinate. Specific examples of the carboxylic acid salt include higher fatty acid salts and polyoxyalkylene alkyl ether acetic acid salts. Specific examples of the phosphoric acid ester salt include alkyl phosphoric acid salts and polyoxyalkylene alkyl ether phosphoric acid salts. Specific examples of the amino acid salt include acyl glutamic acid salts, alanine derivatives, glycine derivatives and arginine derivatives.

Among these anionic surfactants, from the viewpoints of attaining excellent run fingers through hair, coating feel and manageability of hair treated with the hair cosmetic composition after drying, preferred are alkyl sulfuric acid salts, polyoxyethylene alkyl ether sulfuric acid salts, polyoxyethylene alkenyl ether sulfuric acid salts, higher fatty acid salts, polyoxyethylene alkyl ether acetic acid salts, sulfosuccinic acid alkyl ester salts and acyl glutamic acid salts, and especially preferred are polyoxyethylene alkyl ether sulfuric acid salts or alkyl sulfuric acid salts represented by the following general formula (4) or (5).

$$\{R^7-O(CH_2CH_2O)_r SO_3\}_t M \qquad (4)$$

or

$$\{R^8-OSO_3\}_t M \qquad (5)$$

wherein $R^7$ is an alkyl group or alkenyl group having 10 to 18 carbon atoms; $R^8$ is an alkyl group having 10 to 18 carbon atoms; M is an alkali metal, an alkali earth metal, ammonium, a salt of an alkanol amine or a basic amino acid; r represents an average molar number of addition of ethyleneoxy groups, and is a number of 1 to 5; and t is the same number as a valence number of M.

Examples of the nonionic surfactant include polyalkylene glycol-type nonionic surfactants such as polyoxyalkylene sorbitan fatty acid esters, polyoxyalkylene sorbitol fatty acid esters, polyoxyalkylene glycerol fatty acid esters, polyoxyalkylene fatty acid esters, polyoxyalkylene alkyl ethers, polyoxyalkylene alkyl phenyl ethers and polyoxyalkylene (hardened) castor oils, polyhydric alcohol-type nonionic surfactants such as sucrose fatty acid esters, polyglycerol alkyl ethers, polyglycerol fatty acid esters and alkyl glycosides, and fatty acid alkanol amides.

From the viewpoints of attaining excellent run fingers through hair, coating feel and manageability of hair treated with the hair cosmetic composition after drying, among these nonionic surfactants, preferred are polyalkylene glycol-type nonionic surfactants such as polyoxyalkylene alkyl ethers, polyoxyalkylene fatty acid esters, polyoxyalkylene sorbitan fatty acid esters and polyoxyalkylene hardened castor oils, and polyhydric alcohol-type nonionic surfactants such as alkyl glycosides.

The preferred polyoxyalkylene alkyl ethers include polyoxyethylene alkyl ethers, polyoxypropylene alkyl ethers, and polyoxyethylene/polyoxypropylene alkyl ethers.

The polyoxyalkylene fatty acid esters are preferably those in which the oxyalkylene group is an oxyethylene group, and the fatty acid is a fatty aid having 8 to 20 carbon atoms.

The polyoxyalkylene sorbitan fatty acid esters are preferably those in which the oxyalkylene group is an oxyethylene group, and the fatty acid is a fatty aid having 8 to 20 carbon atoms.

The polyoxyalkylene hardened castor oils are preferably those in which the oxyalkylene group is an oxyethylene group.

The fatty acid alkanol amides may be in the form of either a monoalkanol amide or a dialkanol amide, and are preferably those containing a hydroxyalkyl group having 2 to 3 carbon atoms. Specific examples of the fatty acid alkanol amides include oleic acid diethanol amide, palm kernel oil fatty acid diethanol amide, coconut oil fatty acid diethanol amide, lauric acid diethanol amide, polyoxyethylene coconut oil fatty acid monoethanol amide, coconut oil fatty acid monoethanol amide, lauric acid monoisopropanol amide, lauric acid monoethanol amide, palm kernel oil fatty acid methyl ethanol amide and coconut oil fatty acid methyl ethanol amide.

As the alkyl glycosides, preferred are polysaccharides having a polymerization degree of 1 to 20 which contains an alkyl chain having 8 to 18 carbon atoms through a glycoside bond. The polymerization degree of the polysaccharides is more preferably from 1 to 10 and still more preferably from 1 to 5. Examples of the sugar constituting the polysaccharides include glucose and galactose. Among these sugars, preferred is glucose. Specific examples of the alkyl glycosides include alkyl glycosides.

Examples of the amphoteric surfactant include betaine-based surfactants and amine oxide-type surfactants. Among these amphoteric surfactants, from the viewpoints of attaining excellent run fingers through hair, coating feel and manageability of hair treated with the hair cosmetic composition after drying, preferred are betaine-based surfactants such as imidazoline-based betaines, alkyl dimethyl aminoacetic acid betaines, fatty acid amide propyl betaines and sulfobetaines, and amine oxide-type surfactants such as alkyl dimethyl amine oxides, and more preferred are alkylcarboxymethylhydroxyethyl imidazolium betaines, fatty acid amide propyl betaines, sulfobetaines such as alkyl hydroxysulfobetaines, alkyl sulfobetaines, fatty acid amide propyl hydroxysulfobetaines and fatty acid amide propyl sulfobetaines, alkyl dimethyl aminoacetic acid betaines, and alkyl dimethyl amine oxides.

The fatty acid amide propyl betaines and alkyl hydroxysulfobetaines preferably contain an alkyl group having 8 to 18 carbon atoms and more preferably 10 to 16 carbon atoms.

Among these fatty acid amide propyl betaines and alkyl hydroxysulfobetaines, especially preferred are lauric acid amide propyl betaine, palm kernel oil fatty acid amide propyl betaine, coconut oil fatty acid amide propyl betaine, lauryl hydroxysulfobetaine, lauryl sulfobetaine, coconut oil fatty acid amide propyl hydroxysulfobetaine, and coconut oil fatty acid amide propyl sulfobetaine.

The alkyl dimethyl amine oxides preferably contain an alkyl group having 8 to 18 carbon atoms and more preferably 10 to 16 carbon atoms. Among these alkyl dimethyl amine oxides, especially preferred are lauryl dimethyl amine oxide and myristyl dimethyl amine oxide.

Examples of the cationic surfactant include quaternary ammonium salts, pyridinium salts or mineral acid salts or organic acid salts of tertiary amines which contain a hydrocarbon group having 12 to 28 carbon atoms whose carbon chain may be intercepted by an amide group, an ester group or an ether group. Specific examples of the cationic surfactant include mono-long chain alkyl trimethyl ammonium chlorides such as cetyl trimethyl ammonium chloride, stearyl trimethyl ammonium chloride, behenyl trimethyl ammonium chloride and octadecyloxypropyl trimethyl ammonium chloride; di-long chain alkyl dimethyl ammonium chlorides such as distearyl dimethyl ammonium chloride and diisotetradecyl dimethyl ammonium chloride; and mono-long chain alkyl dimethyl amine salts such as hydrochlorides, citrates or lactates of stearyl dimethyl amine, behenyl dimethyl amine and octadecyloxypropyl dimethyl amine.

Among these cationic surfactants, from the viewpoints of attaining excellent run fingers through hair, coating feel and manageability of hair treated with the hair cosmetic composition after drying, preferred are the mono-long chain alkyl trimethyl ammonium chlorides and mono-long chain alkyl dimethyl amine salts.

As the surfactant, there is preferably used at least one surfactant selected from the group consisting of alkyl sulfuric acid salts, polyoxyethylene alkyl ether sulfuric acid salts, polyoxyethylene alkyl ether acetic acid salts, sulfosuccinic acid alkyl ester salts, acyl glutamic acid salts, higher fatty acid salts, polyoxyalkylene alkyl ethers, polyoxyethylene hardened castor oils, fatty acid alkanol amides, alkyl glycosides, alkyl hydroxysulfobetaines, fatty acid amide propyl betaines, alkyl dimethylaminoacetic acid betaines, alkyl amine oxides, alkyl trimethyl ammonium salts and alkyl dimethyl amine salts.

The content of the surfactant in the hair cosmetic composition according to the present invention is preferably from 1 to 80% by mass, more preferably from 1 to 50% by mass and still more preferably from 1 to 20% by mass from the viewpoints of enhancement in run fingers through hair, coating feel and manageability and reduction in sticky or greasy feel of hair treated with the hair cosmetic composition after drying. In the case where the hair cosmetic composition is a shampoo, the content of the surfactant therein is preferably from 5 to 20% by mass and more preferably from 8 to 20% by mass from the same viewpoints. In the case where the hair cosmetic composition is a rinse, a conditioner, a treatment or a hair styling agent, the content of the surfactant therein is preferably from 1 to 10% by mass and more preferably from 1 to 5% by mass from the viewpoints of enhancement in run fingers through hair, coating feel and manageability and reduction in sticky or greasy feel of hair treated with the hair cosmetic composition after drying.

In the hair cosmetic composition according to the present invention, the mass ratio of the C-HPC to the surfactant [C-HPC/surfactant] is preferably from 0.001 to 10, more preferably from 0.003 to 2, still more preferably from 0.005 to 1 and especially preferably from 0.01 to 0.5 from the viewpoints of attaining excellent run fingers through hair, coating feel and manageability of hair treated with the hair cosmetic composition after drying. In the case where the hair cosmetic composition is a shampoo, the mass ratio of the C-HPC to the surfactant [C-HPC/surfactant] is preferably from 0.005 to 0.2, more preferably from 0.01 to 0.1 and especially preferably from 0.02 to 0.05 from the viewpoints of enhancement in run fingers through hair, coating feel and manageability and reduction in sticky or greasy feel of hair treated with the hair cosmetic composition after drying. In the case where the hair cosmetic composition is a rinse, a conditioner, a treatment or a hair styling agent, the mass ratio of the C-HPC to the surfactant [C-HPC/surfactant] is preferably from 0.05 to 1, more preferably from 0.08 to 0.5 and especially preferably from 0.1 to 0.35 from the viewpoints of enhancement in run fingers through hair, coating feel and manageability and reduction in sticky or greasy feel of hair treated with the hair cosmetic composition after drying.

The hair cosmetic composition according to the present invention may also contain a cationic polymer, an amphoteric polymer or an oil component except for the C-HPC of the present invention.

Examples of the cationic polymer or amphoteric polymer include at least one polymer selected from cationic group-containing copolymers as described in JP 3472491, cationized guar gum derivatives as described in JP 58-35640B, JP 60-46158B and JP 58-53996A and cationized hydroxycelluloses as described in JP 4-108723A, as well as diallyl quaternary ammonium salt polymers or diallyl quaternary ammonium salt/acrylamide copolymers represented by the following general formula (6) or (7).

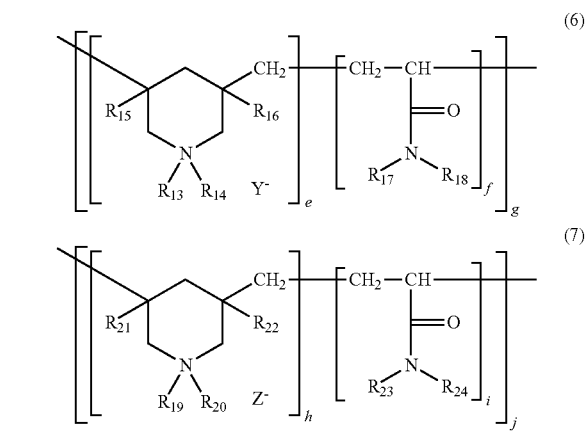

In the above general formula (6) or (7), $R^{13}$, $R^{14}$, $R^{19}$ and $R^{20}$ are each independently a hydrogen atom, an alkyl group having 1 to 18 carbon atoms and preferably 1 to 6 carbon atoms, a phenyl group, an aryl group, a hydroxyalkyl group, an amidoalkyl group, a cyanoalkyl group, an alkoxyalkyl group or a carboalkoxyalkyl group and especially preferably a methyl group; $R^{15}$, $R^{16}$, $R^{21}$ and $R^{22}$ are each independently a hydrogen atom, an alkyl group having 1 to 3 carbon atoms or a phenyl group; and $Y^-$ and $Z^-$ are respectively an anion such as a halogen ion, a sulfuric ion, a sulfonic ion and an alkylsulfuric ion.

The average addition molar numbers e and h are respectively from 1 to 50, the average addition molar numbers f and i are respectively from 0 to 50, and the average addition molar numbers g and j are respectively from 150 to 8000.

Examples of commercially available products of the diallyl quaternary ammonium salt polymers or diallyl quaternary ammonium salt/acrylamide copolymers include "MARCOAT 100" and "MARCOAT 550" both available from Nalco Co.

The content of the cationic polymer or amphoteric polymer except for the C-HPC in the hair cosmetic composition according to the present invention is preferably from 0.01 to 5% by mass, more preferably from 0.05 to 1% by mass and still more preferably from 0.1 to 0.5% by mass.

The mass ratio of the C-HPC to the cationic polymer or amphoteric polymer except for the C-HPC [C-HPC/cationic polymer or amphoteric polymer except for C-HPC] in the hair cosmetic composition according to the present invention is preferably from 0.05 to 20, more preferably from 0.1 to 10, still more preferably from 0.1 to 5 and especially preferably from 0.2 to 1 from the viewpoints of enhancement in run fingers through hair and reduction in sticky or greasy feel of hair treated with the hair cosmetic composition after drying.

Examples of the oil component include higher alcohols, silicones, ester oils, hydrocarbons, glycerides, vegetable oils, animal oils, lanolin derivatives and higher fatty acid esters.

Among these oil components, preferred are higher alcohols, ester oils and silicones, and more preferred are higher alcohols and silicones.

Specific examples of the silicones include those silicones as described in JP 6-48916A.

The hair cosmetic composition may further contain appropriate amounts of various additives such as glycerol, a humectant, polysaccharides, polypeptide, a pearling agent, a solvent, a liquid crystal forming agent, a pigment, a perfume, a propellant, a chelating agent such as ethylenediaminetetraacetic acid salts and citric acid salts, a pH modifier, an antiseptic agent, and an anti-dandruff agent such as zinc pyrithione and piroctone olamine.

The hair cosmetic composition according to the present invention may be produced by an ordinary method. More specifically, for example, in the case of a liquid shampoo, water and the surfactant are heated and uniformly mixed with each other. After confirming that the above components are uniformly dissolved, an oil component or polymer is added to the resulting solution and mixed therewith. The polymer may be added, if required, in the form of a dispersion or a solution prepared by previously dispersing or dissolving the polymer in water. After uniformly dispersed or dissolved, the resulting dispersion or solution is cooled, and then a pearling agent, a pH modifier, a perfume, a pigment, etc., are added thereto, if required, to thereby prepare the liquid shampoo. Similarly, in the case of a conditioner, water and the surfactant are heated and uniformly mixed with each other. Then, a dissolved or melted oil component (such as a higher alcohol) and a solvent are added to emulsify the resulting mixture. Thereafter, the obtained emulsion is cooled, and then an oil component (such as silicone), a pearling agent, a pH modifier, a perfume, a pigment, etc., are added thereto, if required, to thereby prepare the conditioner. The type of the hair cosmetic composition according to the present invention is not particularly limited, and the hair cosmetic composition may be of any optional type including a liquid type, a foam type, a paste type, a cream type, a solid type, a powder type, etc. Among these types, preferred are a liquid type, a paste type and a cream type, and especially preferred is a liquid type.

In order to prepare the hair cosmetic composition of a liquid type, there may be preferably used a liquid medium such as water, polyethylene glycol and ethanol. The amount of water compounded in the hair cosmetic composition is preferably from 10 to 90% by mass on the basis of a whole amount of the composition.

EXAMPLES

In the following Examples and Comparative Examples, "%" as used herein means "% by mass" unless otherwise specified. The methods for measuring various properties used in the following Production Examples and Examples are described in detail below.

(1) Calculation of Crystallinity of Pulp, Powdery Cellulose and Powdery Mixture of Glycidyl Trimethyl Ammonium Chloride and Cellulose The crystallinity of the raw cellulose was determined as follow. That is, an X-ray diffraction spectrum of a sample was measured using a "Rigaku RINT 2500VC X-RAY diffractometer" available from Rigaku Corp., under the following conditions, and a crystallinity of the sample was calculated from a peak intensity in the diffraction spectrum according to the above calculation formula (1).

Measuring Conditions:

X-ray source: Cu/Kα-radiation; tube voltage: 40 kV; tube current: 120 mA; measuring range: diffraction angle 2θ=5 to 45°. The sample to be measured was prepared by compressing pellets each having an area of 320 mm² and a thickness of 1 mm; X-ray scanning speed: 10°/min.

When the thus calculated crystallinity was a negative value, the crystallinity was regarded as being 0%.

(2) Measurement of Average Particle Size of Powdery Cellulose

The average particle size of the powdery cellulose was measured using a laser diffraction/scattering-type particle size distribution measuring device "LA-920" available from Horiba, Ltd. As the sample to be measured, there was used a dispersion prepared by adding 0.1 g of a powdery cellulose to 5 mL of water and treating the resulting mixture with an ultrasonic wave for 1 min. The thus prepared sample was measured for a volume-based median diameter of particles dispersed therein at a temperature of 25° C.

(3) Measurement of Water Content

The water contents of the pulp and the powdery cellulose were respectively measured using an electronic moisture meter "MOC-120H" available from Shimadzu Corp. The measurement was terminated at the point of time at which the rate of change in weight of each sample as measured at 120° C. for 30 s was 0.1% or less.

(4) Calculation of Substitution Degree of C-HPC

The C-HPC produced in the respective Production Examples was purified by passing through a dialysis membrane (cutoff molecular weight: 1000), and then its aqueous solution was freeze-dried to obtain a purified C-HPC. The amount (a (mol/g)) of a cationized ethyleneoxy group (—CH($Y^1$)—CH($Y^2$)O—) in a unit amount of the resulting purified C-HPC was determined as follows. That is, the content (%) of chlorine in the purified C-HPC as a counter ion of the cationic group was measured by elemental analysis, and on the basis of the approximation that the number of the cationic groups contained in the C-HPC is the same as the number of the chlorine ions as a counter ion thereof, the amount of the cationic group was determined from the following calculation formula (2).

$$a\ (\text{mol/g}) = [\text{chlorine content determined from elemental analysis (\%)}]/(35.5 \times 100) \quad (2)$$

Next, the amount (b (mol/g)) of a propyleneoxy group in the C-HPC was determined from a content of a hydroxypropoxy group [molecular weight: $(OC_3H_6OH)=75.09$] therein as measured by "Method for Analysis of Hydroxypropyl Cellulose" as described in the Japanese Pharmacopoeia except that an objective to be analyzed was not hydroxypropyl cellulose but the purified C-HPC according to the following calculation formula (3).

$$b \text{ (mol/g)}=[\text{content of hydroxypropoxy group as measured by gas chromatography (\%)}]/(75.09 \times 100) \quad (3)$$

From the thus calculated values a and b, the cationized ethyleneoxy group substitution degree (k) and the propyleneoxy group substitution degree (m) were calculated according to the following calculation formulae (4) and (5), respectively.

$$a=k/(162+k \times K+m \times 58) \quad (4)$$

and $$b=m/(162+k \times K+m \times 58) \quad (5)$$

wherein k and K represent a cationized ethyleneoxy group substitution degree and a molecular weight thereof, respectively; and m represents a propyleneoxy group substitution degree.

(5) Measurement of Average Polymerization Degree (Copper-Ammonia Method)

(5-1) Measurement of Viscosity-Average Polymerization Degree of Cellulose (i) Preparation of Solution to be Measured A measuring flask (100 mL) was charged with 0.5 g of cuprous chloride and 20 to 30 mL of 25% aqueous ammonia, and after completely dissolving the contents of the flask, 1.0 g of cupric hydroxide and 25% aqueous ammonia were added to the resulting solution such that the flask was filled therewith just before reaching a marked line of the flask. The contents of the flask were stirred for 30 to 40 min and thereby completely dissolved. Thereafter, a cellulose was accurately weighed and added to the resulting solution, and then the aqueous ammonia was filled in the flask until reaching the marked line. The flask was hermetically sealed, and the contents of the flask were stirred for 12 h using a magnetic stirrer and dissolved to prepare a sample solution to be measured. The amount of the cellulose added was varied over the range of from 20 to 500 mg to prepare various sample solutions to be measured which were different in concentration from each other.

(ii) Measurement of Viscosity-Average Polymerization Degree

The solution to be measured (copper-ammonia solution) obtained in the above (i) was filled in an Ubbelohde viscometer, and after the viscometer filled with the solution was allowed to stand in a constant temperature oven (20±0.1° C.) for 1 h, a falling velocity of the solution was measured. The copper-ammonia solutions having various cellulose concentrations (g/dL) were measured for their falling velocity (t (sec)), and a copper-ammonia solution containing no cellulose was also measured for its falling velocity ($t_0$ (sec)). From the thus measured values, a relative viscosity ($\eta_r$) of each solution was calculated according to the following formula.

$$\eta_r = t/t_0$$

Next, a reduced viscosity ($\eta_{sp}/c$) of the solution at the respective concentrations was calculated according to the following formula.

$$\eta_{sp}/c=(\eta_r-1)/c$$

wherein c is a cellulose concentration (g/dL).

In addition, the reduced viscosity was extrapolated at c=0 to determine an intrinsic viscosity [η] (dL/g) thereof, and the viscosity-average polymerization degree (DP) was calculated according to the following formula.

$$DP=2000 \times [\eta]$$

(5-2) Measurement of Viscosity-Average Polymerization Degree of C-HPC (iii) Preparation of Solution to be Measured The solution to be measured was prepared by the same method as described in the above (i) except for using the purified C-HPC in place of the purified cellulose.

(iv) Measurement of Viscosity-Average Polymerization Degree

The viscosity-average polymerization degree was measured by the same method as described in the above (ii) except for using a cellulose-reduced concentration (g/dL) as the concentration of the solution to be measured.

The "cellulose-reduced concentration (g/dL)" ($c_{cell}$) as used herein means a mass (g) of a cellulose skeleton portion contained in 1 dL of the solution to be measured, and defined by the following calculation formula (6).

$$c_{cell}=u \times 162/(162+k \times K+m \times 58) \quad (6)$$

wherein u represents a mass (g) of the purified C-HPC used upon preparing the solution to be measured; and k, K and m respectively represent the same meanings as used in the above calculation formulae (4) and (5).

(5-3) Measurement of Average Polymerization Degree of Hydroxypropyl Cellulose

It was difficult to prepare a solution in which a commercially available hydroxypropyl cellulose ("Celluny M" (tradename) available from Nippon Soda Co., Ltd.) was completely dissolved by the same method as described in the above (i). Therefore, the average polymerization degree of the commercially available hydroxypropyl cellulose was determined by the method described in "Food Technology", Vol. 24, p. 54.

Production Example 1

Production of C-HPC (1)

(1) Production of Low-Crystalline Powdery Cellulose

A sheet-like wood pulp ("Biofloc HV+" available from Tembec Inc.; crystallinity: 76%; average polymerization degree: 1550; water content: 7%) was cut into chips using a shredder "MSX2000-IVP440F" available from Meiko Shokai Co., Ltd. Then, the thus obtained pulp chips were dried under reduced pressure at 50° C. for 12 h, thereby obtaining a chip-like dry pulp (water content: 0.4%).

Next, 100 g of the thus obtained chip-like dry pulp were charged into a batch-type vibration mill "MB-1" available from Chuo Kakoki Co., Ltd., having a total container capacity of 3.5 L which was filled with thirteen SUS304 rods of ϕ30 mm and a length of 218 mm having a circular shape in section at a filling percentage of 57%. The chip-like dry pulp was pulverized in the vibration mill at a frequency of 20 Hz and a total amplitude of 8 mm at a temperature of from 30 to 70° C. for 20 min, thereby obtaining a powdery cellulose (crystallinity: 0%; average polymerization degree: 836; average particle size: 52 μm; water content: 1%).

(2) Cationization Reaction

A 1-L kneader "PNV-1 Model" (available from Irie Shokai Co., Ltd.) equipped with a reflux tube was charged with 100 g of the powdery cellulose obtained in the above (1), and then 10.2 g of a 48% sodium hydroxide aqueous solution (NaOH content: 0.12 mol) were added dropwise thereto while stirring, and the contents of the kneader were stirred in a nitrogen atmosphere for 3 h. Thereafter, the kneader was heated to 70° C. by a warm water, and then 16.8 g of an aqueous solution of glycidyl trimethyl ammonium chloride (hereinafter referred to merely as "GMAC"; available from Sakamoto Yakuhin Kogyo Co., Ltd.; water content: 20%; purity: 90% or more) as a cationizing agent whose water content was previously adjusted to 38.5% by adding water thereto were added dropwise into the kneader over 1 h while stirring. Then, the contents of the kneader were further stirred at 70° C. for 3 h. As a result of analysis by high-pressure liquid chromatography (HPLC), it was confirmed that a whole amount of the cationizing agent added was consumed.

(3) Hydroxypropylation Reaction

Next, while heating the cationized cellulose obtained in the above (2) at 70° C., 70.9 g of propyleneoxide (1.22 mol; available from Kanto Chemical Co., Inc.; guaranteed reagent) were added dropwise thereto while stirring, and the contents in the kneader were reacted for 16 h until the propyleneoxide added was consumed and the reflux was terminated. After completion of the reaction, the resulting cellulose was kept in a fluidized powder state. The thus obtained final reaction product was sampled in an amount of 10.0 g and neutralized with acetic acid, thereby obtaining a light brown solid. The resulting product was purified by passing through a dialysis membrane (cutoff molecular weight: 1000), and then its aqueous solution was freeze-dried to obtain C-HPC (1).

As a result of subjecting the thus obtained C-HPC (1) to elemental analysis, it was confirmed that the chlorine element content therein was 1.2%. Further, as a result of analyzing the product by the method for analysis of hydroxypropyl cellulose, it was confirmed that the content of a hydroxypropoxy group [molecular weight $(OC_3H_6OH)=75.09$] therein was 48.2%. Furthermore, it was confirmed that the cationized ethyleneoxy group substitution degree and the propyleneoxy group substitution degree were 0.09 and 1.8, respectively. The average polymerization degree of the C-HPC (1) (average polymerization degree of the powdery cellulose used for production thereof) as well as the cationized ethyleneoxy group substitution degree and the propyleneoxy group substitution degree of the C-HPC (1) are shown in Table 3.

Production Examples 2 to 6

C-HPC's (2) to (6)

The same procedure as in Production Example 1 was repeated except that a pulp having a different polymerization degree was used as the raw material, and the use or non-use of drying step after being chipped, the mill treatment time, or the amounts of GMAC and propyleneoxide added were varied. The production conditions as well as the chlorine content (%) and hydroxypropoxy group content (%) of the obtained C-HPC's are shown in Table 1.

The average polymerization degree, the cationized ethyleneoxy group substitution degrees and the propyleneoxy group substitution degrees of the resulting C-HPC's (2) to (6) are shown in Table 3.

Production Example 7

Production of C-HPC (7)

(1) Production of Amorphized Powdery Cellulose

A sheet-like wood pulp ("Blue Bear Ultra Ether" available from Borregaard Inc.; crystallinity: 79%; average polymerization degree: 1532; water content: 7%) was cut into chips using a shredder "MSX2000-IVP440F" available from Meiko Shokai Co., Ltd.

Then, the thus obtained pulp chips were charged into a twin-screw extruder "EA-20" available from Suchiro EPM Corp., at a feed rate of 2 kg/h and passed through the extruder one time at a shear rate of 660 $\sec^{-1}$ and a screw rotating speed of 300 rpm while flowing a cooling water from outside therethrough to obtain a powder.

Next, 100 g of the thus obtained powdery cellulose (water content: 7%) were charged into a batch-type medium-stirring mill "ATTRITOR MA01D" available from Nippon Coke & Engineering Co., Ltd., having a container capacity of 800 mL which was filled with 1440 g of φ¼ in. SUS304 balls at a filling percentage of 23% and fitted with an agitation blade having a diameter of 65 mm. While flowing a cooling water through a jacket of the container, the powdery cellulose was pulverized at a stirring speed of 555 rpm and a temperature of from 30 to 70° C. for 7 h, thereby obtaining a powdery cellulose (crystallinity: 0%; average polymerization degree: 556; average particle size: 30 μm; water content: 7%).

(2) Hydroxypropylation Reaction

A 1-L kneader "PNV-1 Model" (available from Irie Shokai Co., Ltd.) equipped with a reflux tube was charged with 100 g of the powdery cellulose obtained in the above (1), and then 9.6 g of a 48% sodium hydroxide aqueous solution (NaOH content: 0.12 mol) were added dropwise thereto while stirring, and the contents of the kneader were stirred in a nitrogen atmosphere for 3 h. Thereafter, the kneader was heated to 70° C. by a warm water, and then 40.0 g of propyleneoxide (0.69 mol) were added dropwise thereto while stirring, and the contents in the kneader were reacted for 7 h until the propyleneoxide added was consumed and the reflux was terminated.

(3) Cationization Reaction

Next, while heating the hydroxypropylated cellulose obtained in the above (2) at 70° C., 62.9 g of GMAC (available from Sakamoto Yakuhin Kogyo Co., Ltd.; water content: 20%; purity: 90% or more) were added dropwise into the kneader over 3 h while stirring. Then, the contents of the kneader were further stirred at 70° C. for 3 h. As a result of analysis by high-pressure liquid chromatography (HPLC), it was confirmed that a whole amount of the cationizing agent added was consumed. The thus obtained final reaction product was sampled in an amount of 10.0 g and neutralized with acetic acid, thereby obtaining a light brown solid. The resulting product was purified by passing through a dialysis membrane (cutoff molecular weight: 1000), and then its aqueous solution was freeze-dried to obtain C-HPC (7).

As a result of subjecting the thus obtained C-HPC (7) to elemental analysis, it was confirmed that the chlorine element content therein was 3.7%. Further, as a result of analyzing the product by the method for analysis of hydroxypropyl cellulose, it was confirmed that the content of a hydroxypropoxy group [molecular weight $(OC_3H_6OH)=75.09$] therein was 28.7%. The results are shown in Table 2.

Furthermore, it was confirmed that the cationized ethyleneoxy group substitution degree and the propyleneoxy group substitution degree of the C-HPC (7) were 0.27 and 1.0, respectively. The average polymerization degree of the C-HPC (7) (average polymerization degree of the powdery cellulose used for production thereof) as well as the cationized ethyleneoxy group substitution degree and the propyleneoxy group substitution degree of the C-HPC (7) are shown in Table 3.

Production Examples 8 to 10

C-HPC's (8) to (10)

The same procedure as in Production Example 7 was repeated except that the amounts of GMAC and propyleneoxide added were varied. The production conditions as well as the chlorine content (%) and hydroxypropoxy group content (%) of the obtained C-HPC's are shown in Table 2.

The average polymerization degrees, the cationized ethyleneoxy group substitution degrees and the propyleneoxy group substitution degrees of the resulting C-HPC's (8) to (10) are shown in Table 3.

TABLE 1-1

|  | Shredder milling step Drying step | Chip-like dried pulp Water content (%) | Milling step Milling time | Powdery cellulose Crystallinity (%) | Average polymerization degree | Average particle size (μm) | Water content (%) |
|---|---|---|---|---|---|---|---|
| Production Example 1*[1] | 50° C. under reduced pressure for 12 h | 0.4 | 20 min | 0 | 836 | 52 | 1 |
| Production Example 2*[2] | None | — | 1 h | 0 | 574 | 31 | 7 |
| Production Example 3*[2] | None | — | 2 h | 0 | 392 | 18 | 7 |
| Production Example 4*[2] | 50° C. under reduced pressure for 12 h | 0.4 | 20 min | 0 | 760 | 34 | 1 |
| Production Example 5*[1] | 50° C. under reduced pressure for 12 h | 0.4 | 20 min | 0 | 836 | 52 | 1 |
| Production Example 6*[1] | 50° C. under reduced pressure for 12 h | 0.4 | 20 min | 0 | 836 | 52 | 1 |

Note
*[1]"Biofloc HV+" available from Tembec Inc., was used as the raw material pulp.
*[2]"Biofloc HV-10A" available from Tembec Inc., was used as the raw material pulp.

TABLE 1-2

|  | Cationization reaction step | | Hydroxypropylation reaction step | C-HPC | |
|---|---|---|---|---|---|
|  | Amount of 48% NaOH aqueous solution added (g) | Amount of GMAC aqueous solution added (g) | Amount of propyleneoxide added (g) | Chlorine content (%) | Hydroxypropoxy group content (%) |
| Production Example 1*[1] | 10.2 | 16.8 | 70.9 | 1.2 | 48.2 |
| Production Example 2*[2] | 9.6 | 15.8 | 99.9 | 1.0 | 57.2 |
| Production Example 3*[2] | 9.6 | 15.8 | 99.9 | 1.0 | 59.5 |
| Production Example 4*[2] | 10.2 | 16.8 | 106.5 | 0.9 | 62.3 |
| Production Example 5*[1] | 10.2 | 33.6 | 53.2 | 2.3 | 37.0 |
| Production Example 6*[1] | 10.2 | 33.6 | 88.6 | 2.0 | 50.8 |

TABLE 2

|  | Hydroxypropylation reaction step | | Cationization reaction step | C-HPC | |
|---|---|---|---|---|---|
|  | Amount of 48% NaOH aqueous solution added (g) | Amount of propyleneoxide added (g) | Amount of GMAC aqueous solution added (g) | Chlorine content (%) | Hydroxypropoxy group content (%) |
| Production Example 7 | 9.6 | 40 | 62.9 | 3.7 | 28.7 |
| Production Example 8 | 9.6 | 83.2 | 120.9 | 2.7 | 51.3 |
| Production Example 9 | 9.6 | 133.2 | 120.9 | 1.0 | 67.7 |
| Production Example 10 | 9.6 | 115.0 | 190.0 | 1.0 | 65.1 |

TABLE 3

| | | Average polymerization degree*1 | Cationized EO substitution degree*2 | PO substitution degree*3 |
|---|---|---|---|---|
| Production Example 1 | C-HPC (1) | 836 | 0.09 | 1.8 |
| Production Example 2 | C-HPC (2) | 574 | 0.09 | 2.4 |
| Production Example 3 | C-HPC (3) | 392 | 0.09 | 2.6 |
| Production Example 4 | C-HPC (4) | 760 | 0.09 | 2.8 |
| Production Example 5 | C-HPC (5) | 836 | 0.17 | 1.3 |
| Production Example 6 | C-HPC (6) | 836 | 0.17 | 2.1 |
| Production Example 7 | C-HPC (7) | 556 | 0.27 | 1.0 |
| Production Example 8 | C-HPC (8) | 556 | 0.25 | 2.3 |
| Production Example 9 | C-HPC (9) | 556 | 0.10 | 3.4 |
| Production Example 10 | C-HPC (10) | 556 | 0.10 | 3.1 |

Note
*1 Average polymerization degree of amorphized powdery cellulose used as a raw material in the reaction.
*2 Cationized ethyleneoxy group substitution degree
*3 Propyleneoxy group substitution degree

Production Example 11

Production of C-HPC (11)

(1) Chipping

A sheet-like wood pulp (available from Tembec Inc.; average polymerization degree: 1508; crystallinity: 74%; water content: 7.6%) was cut into chips using a sheet pelletizer "SGG-220" available from Horai Co., Ltd.

(2) Cationization Reaction

Next, 2100 g of the thus obtained chip-like pulp were mixed with 1170 g of GMAC (available from Sakamoto Yakuhin Kogyo Co., Ltd.; water content: 20.0%; purity: 90% or more) using a mortar, and the resulting mixture was charged into a batch-type vibration mill "FV-20" available from Chuo Kakoki Co., Ltd., having a total container capacity of 69 L which was filled with one hundred fourteen SUS304 rods of ϕ30 mm and a length of 600 mm having a circular shape in section at a filling percentage of 71%. The chip-like pulp was pulverized in the vibration mill at a frequency of 60 Hz and an amplitude of 8 mm at a temperature of from 10 to 40° C. for 12 min, thereby obtaining a mixture of the cellulose and GMAC.

Further, 284 g of sodium hydroxide (effective content: 100%) were charged into the vibration mill, and the contents of the mill were pulverized again for 120 min, thereby obtaining a cationized cellulose.

(3) Hydroxypropylation Reaction

The kneader charged with 170 g of the cationized cellulose obtained in the above step was heated to 70° C., and then 66.6 g of propyleneoxide were added dropwise thereto while stirring, and the contents in the kneader were reacted for 6 h until the propyleneoxide added was consumed and the reflux was terminated.

The reaction mixture finally obtained after the reaction was taken out of the kneader to obtain 223.3 g of a light brown crude C-HPC powder. The thus obtained final reaction product was sampled in an amount of 10.0 g and neutralized with lactic acid, thereby obtaining a light brown solid. For the purpose of determining the propyleneoxy group substitution degree and the cationized ethyleneoxy group substitution degree, the resulting product was purified by passing through a dialysis membrane (cutoff molecular weight: 1000), and then its aqueous solution was freeze-dried to obtain C-HPC (11).

As a result of subjecting the thus obtained C-HPC (11) to elemental analysis, it was confirmed that the chlorine element content therein was 2.5%. Further, as a result of analyzing the product by the method for analysis of hydroxypropyl cellulose, it was confirmed that the content of a hydroxypropoxy group [molecular weight $(OC_3H_6OH)=75.09$] therein was 34.8%. The results are shown in Table 4.

Furthermore, the calculated values of the cationized ethyleneoxy group substitution degree and the propyleneoxy group substitution degree were 0.18 and 1.2, respectively. The average polymerization degree of the C-HPC (11) was 1302. The results are shown in Table 6.

Production Examples 12, 13, 16, 18 and 20

C-HPC's (12), (13), (16), (18) and (20)

The same procedure as in Production Example 11 was repeated except that the amounts of GMAC and sodium hydroxide added upon the cationization reaction, the vibration mill apparatus, and the amounts of the cationized cellulose and propyleneoxide added upon the hydroxypropylation reaction were varied. The production conditions as well as the chlorine content (%) and hydroxypropoxy group content (%) of the obtained C-HPC's are shown in Table 4.

The average polymerization degrees, the cationized ethyleneoxy group substitution degrees and the propyleneoxy group substitution degrees of the resulting C-HPC's (12), (13), (16), (18) and (20) are shown in Table 6.

Production Example 14

Production of C-HPC (14)

(1) Chipping

A sheet-like wood pulp (available from Tembec Inc.; average polymerization degree: 1770; crystallinity: 74%; water content: 7.0%) was cut into chips using a sheet pelletizer "SGG-220" available from Horai Co., Ltd.

(2) Cationization Reaction (1)

Next, 100 g of the thus obtained chip-like pulp were mixed with 23.4 g of GMAC (available from Sakamoto Yakuhin Kogyo Co., Ltd.; water content: 20.0%; purity: 90% or more) using a mortar, and the resulting mixture was charged into the vibration mill as used in Production Example 1. The chip-like pulp was pulverized in the vibration mill at a frequency of 60 Hz and an amplitude of 8 mm at a temperature of from 10 to 40° C. for 30 min, thereby obtaining a mixture of the cellulose and GMAC.

Further, 10.3 g of a 48% sodium hydroxide aqueous solution were charged into the vibration mill, and the contents of the mill were pulverized again for 60 min, thereby obtaining a cationized cellulose.

(3) Hydroxypropylation Reaction

The kneader charged with 127 g of the cationized cellulose obtained in the above step was heated to 70° C., and then 53.9 g of propyleneoxide were added dropwise thereto while stirring, and the contents in the kneader were reacted for 6 h until the propyleneoxide added was consumed and the reflux was terminated.

(4) Cationization Reaction (2)

The reaction mixture finally obtained after the reaction was transferred from the kneader to a mortar, and then 70.1 g of GMAC were added thereto, and further the resulting mixture was mixed at room temperature for 10 min. Thereafter, the mixture was charged back into the kneader and reacted therein at 50° C. for 5 h while stirring, thereby obtaining 248.0 g of a light brown crude C-HPC powder. The thus obtained final reaction product was sampled in an amount of 10.0 g and neutralized with lactic acid, thereby obtaining a light brown solid. For the purpose of determining the propyleneoxy group substitution degree and the cationized ethyleneoxy group substitution degree, the resulting product was purified by passing through a dialysis membrane (cutoff molecular weight: 1000), and then its aqueous solution was freeze-dried to obtain C-HPC (14).

As a result of subjecting the thus obtained C-HPC (14) to elemental analysis, it was confirmed that the chlorine element content therein was 5.5%. Further, as a result of analyzing the product by the method for analysis of hydroxypropyl cellulose, it was confirmed that the content of a hydroxypropoxy group [molecular weight $(OC_3H_6OH)=75.09$] therein was 28.4%. The results are shown in Table 5.

Furthermore, the calculated values of the cationized ethyleneoxy group substitution degree and the propyleneoxy group substitution degree were 0.53 and 1.7, respectively. The average polymerization degree of the C-HPC (14) was 744. The results are shown in Table 6.

Production Examples 15, 17 and 19

C-HPC's (15), (17) and (19)

The same procedure as in Production Example 14 was repeated except that the kind of raw material pulp, the amounts of GMAC and sodium hydroxide added upon the cationization reactions (1) and (2), the mill treatment time, and the amounts of the cationized cellulose and propyleneoxide added upon the hydroxypropylation reaction were varied, and the same drying treatment as in Production Example 1 was conducted before the cationization reaction (1). The production conditions as well as the chlorine content (%) and hydroxypropoxy group content (%) of the obtained C-HPC are shown in Table 5.

The average polymerization degrees, the cationized ethyleneoxy group substitution degrees and the propyleneoxy group substitution degrees of the resulting C-HPC's (15), (17) and (19) are shown in Table 6.

TABLE 4-1

| | Raw material pulp Amount of pulp used (g) | Vibration mill | Cationization reaction step | | | |
|---|---|---|---|---|---|---|
| | | | Amount of 80% GMAC aqueous solution added (g) | Milling time (min) | Amount of NaOH added (g) | Milling time (min) |
| Production 11 | 2100 | FV-20 | 1170 | 12 | 284 | 120 |
| Production 12 | 2100 | FV-20 | 1170 | 12 | 284 | 120 |
| Production 13 | 1013 | FV-10*[1] | 559 | 12 | 136 | 112 |
| Production 16 | 100 | MB-1*[2] | 11.3 | 12 | 22.8 | 160 |
| Production 18 | 100 | MB-1*[2] | 109 | 12 | 23 | 120 |
| Production 20*[3] | 100 | MB-1*[2] | 2.0 | 12 | 23 | 40 |

Note
*[1] "FV-10" available from Chuo Kakoki Co., Ltd.; total container capacity: 35 L; filled with sixty three SUS304 rods of φ30 mm and a length of 510 mm having a circular shape in section at a filling percentage of 64%.
*[2] Vibration mill described in Example 1.
*[3] Ten grams of water were added before adding propyleneoxide.

TABLE 4-2

| | Hydroxypropylation reaction step | | C-HPC | |
|---|---|---|---|---|
| | Amount of cationized cellulose used (g) | Amount of propyleneoxide used (g) | Chlorine content (%) | Hydroxypropoxy group content (%) |
| Production 11 | 170 | 66.6 | 2.5 | 34.8 |
| Production 12 | 170 | 99.9 | 2.1 | 52.1 |
| Production 13 | 170 | 66.6 | 4.0 | 26.3 |
| Production 16 | 127 | 33.3 | 0.5 | 30.6 |
| Production 18 | 220 | 153 | 3.3 | 54.4 |
| Production 20*[3] | 170 | 66.6 | 0.09 | 33.2 |

TABLE 5-1

| | Chipping step | Drying step | | Cationization reaction (1) step | | | |
|---|---|---|---|---|---|---|---|
| | | Conditions | Water content after drying (%) | Amount of 80% GMAC aqueous solution added (g) | Milling time (min) | Amount of NaOH aqueous solution added (g) | Milling time (min) |
| Production 14 | Done | — | — | 23.4 | 30 | 10.3 | 60 |
| Production 15 | Done | 50° C. under reduced pressure for 12 h | 1 | 23.4 | 12 | 10.3 | 60 |

TABLE 5-1-continued

| | Chipping step | Drying step Conditions | Drying step Water content after drying (%) | Cationization reaction (1) step Amount of 80% GMAC aqueous solution added (g) | Cationization reaction (1) step Milling time (min) | Cationization reaction (1) step Amount of NaOH aqueous solution added (g) | Cationization reaction (1) step Milling time (min) |
|---|---|---|---|---|---|---|---|
| Production 17*[1] | None | 50° C. under reduced pressure for 12 h | 1 | 60.8 | 12 | 29.8 | 140 |
| Production 19*[1] | None | 50° C under reduced pressure for 12 h | 1 | 23.4 | 12 | 10.3 | 60 |

Note
*[1]"KC-W400G" available from Nippon Paper Chemicals Co., Ltd., (powdery cellulose) was used as a raw material pulp.

TABLE 5-2

| | Hydroxypropylation reaction step Amount of cationized cellulose used (g) | Hydroxypropylation reaction step Amount of propyleneoxide added (g) | Cationization reaction (2) step Amount of 80% GMAC aqueous solution added (g) | C-HPC Chlorine content (%) | C-HPC Hydroxypropoxy group content (%) |
|---|---|---|---|---|---|
| Production 14 | 127 | 53.9 | 70.1 | 5.5 | 37.5 |
| Production 15 | 127 | 35.9 | 152 | 9.3 | 5.3 |
| Production 17*[1] | 190 | 18.0 | 87.5 | 15.7 | 3.3 |
| Production 19*[1] | 127 | 35.9 | 152 | 9.5 | 1.4 |

TABLE 6

| | | Average polymerization degree of C-HPC obtained | Cationized EO substitution degree*[1] | PO substitution degree*[2] |
|---|---|---|---|---|
| Production Example 11 | C-HPC (11) | 1302 | 0.18 | 1.2 |
| Production Example 12 | C-HPC (12) | 1302 | 0.18 | 2.2 |
| Production Example 13 | C-HPC (13) | 575 | 0.29 | 0.9 |
| Production Example 14 | C-HPC (14) | 744 | 0.53 | 1.7 |
| Production Example 15 | C-HPC (15) | 1326 | 0.75 | 0.2 |
| Production Example 16 | C-HPC (16) | 926 | 0.03 | 0.9 |
| Production Example 17 | C-HPC (17) | 432 | 2.36 | 0.2 |
| Production Example 18 | C-HPC (18) | 964 | 0.35 | 2.7 |
| Production Example 19 | C-HPC (19) | 179 | 0.75 | 0.05 |
| Production Example 20 | C-HPC (20) | 759 | 0.005 | 1.0 |

Note
*[1]Cationized ethyleneoxy group substitution degree
*[2]Propyleneoxy group substitution degree Evaluation of Hair Cosmetic Compositions Examples 1 to 17

Production and Evaluation of Shampoos

The shampoos having compositions in which the respective components were contained in effective amounts as shown in Table 7 were produced from the C-HPC's (1) to (8) and (11) to (18), and sodium polyoxyethylene alkylsulfate ("EMAL 270J" (tradename) available from Kao Corp.; 70% aqueous solution; average molar number of addition of oxyethylene groups: 2; alkyl chain length; C10 to 16) and coconut oil fatty acid amide propyl carbobetaine ("AMPHITOL 55AB" (tradename) available from Kao Corp.; 30% aqueous solution) both serving as a surfactant, by an ordinary method. More specifically, the C-HPC or cationized guar gum was dissolved or uniformly dispersed in water to prepare a 2% polymer solution. Separately, the respective components except for the polymer were placed in a beaker, heated to 80° C., and then stirred and uniformly dissolved. Then, the polymer solution was added to the resulting solution and uniformly mixed therewith, and the obtained mixed solution was cooled. Finally, water was added to the solution to replenish an amount of water evaporated therefrom by heating, and then the pH value of the solution was measured. The pH value of the solution was adjusted by adding a 50% citric acid aqueous solution or a 48% sodium hydroxide aqueous solution (hereinafter also referred to as a "pH modifier") thereto, if required.

The respective components having the following composition were placed in a beaker, and heated to 80° C. and then mixed with each other. After confirming that the respective components were uniformly dissolved, the resulting solution was cooled to thereby obtain a plain shampoo. The thus obtained plain shampoo was used to wash a hair bundle. Then, the hair bundle was sufficiently wetted with warm water at a temperature of 35 to 40° C., washed with the shampoo having a composition shown in Table 7, rinsed with warm water and wiped with a towel to remove water therefrom, and then set by combing. Thereafter, the hair bundle was dried by a warm air from a dryer and finished by setting with a comb. The thus treated hair bundle was used as tresses to be evaluated, and evaluation of stickiness, run fingers through hair, coating feel and manageability of hair was performed by 5 panelists by the following evaluation method according to the following evaluation ratings. The results are shown in Table 7.

(Composition of Plain Shampoo)

| (Components) | (%) |
|---|---|
| Sodium (Na) polyoxyethylenelaurylethersulfate ("EMAL E-27C" (available from Kao Corp.; effective content: 27% by weight): 42.0%) | 11.3 |
| Coconut oil fatty acid N-methyl ethanol amide ("AMINONE C-11S" available from Kao Corp.) | 3.0 |
| Citric acid | 0.2 |
| Methyl paraben (methyl 4-hydroxybenzoate) | 0.3 |
| Purified water | balance |
| Total | 100.0 |

(Evaluation Ratings)
Stickiness
  5: No stickiness
  4: Less stickiness
  3: Normal
  2: Slight stickiness
  1: Severe stickiness
Run fingers through hair
  5: Excellent
  4: Good
  3: Normal
  2: Not good
  1: Poor
Coating feel
  5: Excellent coating feel
  4: Good coating feel
  3: Normal
  2: Less coating feel
  1: No coating feel
Manageability (less dryness of hair)
  5: Very good manageability of hair
  4: Good manageability of hair
  3: Normal
  2: Dryness of hair with less manageability
  1: Severe dryness of hair without any manageability
(Evaluation Method)
The score number of the respective evaluation items was determined from an average value of the evaluation results of the 5 panelists.

Comparative Examples 1 to 8

Production and Evaluation of Shampoos

The respective shampoos having compositions shown in Table 7 were produced from the C-HPC's (9), (10), (19) and (20), a cationized hydroxyethyl cellulose ("MARCOAT 10" (tradename) available from Nalco Co.), a cationized guar gum ("JAGUAR C-13S" (tradename) available from Rhodia Corp.) and hydroxypropyl cellulose ("CELNY M" (tradename) available from Nippon Soda Co., Ltd.) and evaluated by the same method as in Example 1. The results are collectively shown in Table 7.

TABLE 7-1

| Hair cosmetic composition (shampoo) | Examples | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Formulation (part(s) by mass) | | | | | | | | | | | | | | | | | |
| C-HPC (1) | 0.5 | | | | | | | | | | | | | | | | |
| C-HPC (2) | | 0.5 | | | | | | | | | | | | | | | |
| C-HPC (3) | | | 0.5 | | | | | | | | | | | | | | |
| C-HPC (4) | | | | 0.5 | | | | | | | | | | | | | |
| C-HPC (5) | | | | | 0.5 | | | | | | | | | | | | |
| C-HPC (6) | | | | | | 0.5 | | | | | | | | | | | |
| C-HPC (7) | | | | | | | 0.5 | | | | | | | | | | |
| C-HPC (8) | | | | | | | | 0.5 | | | | | | | | | |
| C-HPC (11) | | | | | | | | | 0.2 | 0.5 | | | | | | | |
| C-HPC (12) | | | | | | | | | | | | 0.5 | | | | | |
| C-HPC (13) | | | | | | | | | | | | | 0.5 | | | | |
| C-HPC (14) | | | | | | | | | | | | | | 0.5 | | | |
| C-HPC (15) | | | | | | | | | | | | | | | 0.5 | | |
| C-HPC (16) | | | | | | | | | | | | | | | | 0.5 | |
| C-HPC (17) | | | | | | | | | | | | | | | | | 0.5 |
| C-HPC (18) | | | | | | | | | | | | | | | | | 0.5 |
| C-HPC (9) | | | | | | | | | | | | | | | | | |
| C-HPC (10) | | | | | | | | | | | | | | | | | |
| C-HPC (19) | | | | | | | | | | | | | | | | | |
| C-HPC (20) | | | | | | | | | | | | | | | | | |
| Cationized hydroxyethyl cellulose 1 *[1] | | | | | | | | | | | | | | | | | |
| Cationized guar gum *[2] | | | | | | | | | | 0.3 | | | | | | | |
| Hydroxypropyl cellulose *[3] | | | | | | | | | | | | | | | | | |
| Sodium polyoxyethylene (2) alkylethersulfate *[4] | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 | 7.5 |
| Coconut oil fatty acid amide propyl betaine *[5] | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| Sodium chloride | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 | 1.0 |
| pH Modifier | | | | | | | | | | | q.s. | | | | | | |
| Purified water | | | | | | | | | | | balance | | | | | | |
| pH (diluted 20 times; 25° C.) | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 | 6.0 |
| Evaluation | | | | | | | | | | | | | | | | | |
| Stickiness | 5 | 5 | 5 | 5 | 5 | 5 | 5 | 5 | 4.8 | 5 | 5 | 5 | 5 | 5 | 5 | 5 | 5 |
| Run fingers through hair | 4.6 | 4.6 | 4.4 | 4.4 | 4.8 | 4.4 | 4.4 | 4.4 | 4.8 | 5 | 4.8 | 4.8 | 5 | 4.2 | 4 | 4.8 | 4.2 |

TABLE 7-1-continued

| Hair cosmetic composition (shampoo) | Examples | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| Coating feel | 4.6 | 4 | 4.2 | 4.6 | 4.6 | 4.6 | 4.2 | 4 | 5 | 5 | 4.8 | 4.6 | 4.8 | 3.8 | 4 | 4.2 | 4.4 |
| Manageability | 4.8 | 4.6 | 4.2 | 4 | 4.8 | 4.6 | 4.8 | 4.6 | 4.8 | 4.8 | 4.8 | 4.8 | 4.6 | 4 | 4 | 3.8 | 4 |

Note
*[1] "MARCOAT 10" available from Nalco Co.;
*[2] "JAGUAR C-13S" available from Rhodia Corp.;
*[3] "CELNY M" available from Nippon Soda Co., Ltd.;
*[4] "EMAL 270S" available from Kao Corp. (effective content: 70%); added in an amount of 10.7%;
*[5] "AMPHITOL 55AB" available from Kao Corp. (effective content: 30%); added in an amount of 15%

TABLE 7-2

| Hair cosmetic composition (shampoo) | Comparative Examples | | | | | | | |
|---|---|---|---|---|---|---|---|---|
| | 1 | 2 | 3 | 4 | 5 | 6 | 7 | 8 |
| Formulation (part(s) by mass) | | | | | | | | |
| C-HPC (1) | | | | | | | | |
| C-HPC (2) | | | | | | | | |
| C-HPC (3) | | | | | | | | |
| C-HPC (4) | | | | | | | | |
| C-HPC (5) | | | | | | | | |
| C-HPC (6) | | | | | | | | |
| C-HPC (7) | | | | | | | | |
| C-HPC (8) | | | | | | | | |
| C-HPC (11) | | | | | | | 0.5 | |
| C-HPC (12) | | | | | | | | |
| C-HPC (13) | | | | | | | | |
| C-HPC (14) | | | | | | | | |
| C-HPC (15) | | | | | | | | |
| C-HPC (16) | | | | | | | | |
| C-HPC (17) | | | | | | | | |
| C-HPC (18) | | | | | | | | |
| C-HPC (9) | 0.5 | | | | | | | |
| C-HPC (10) | | 0.5 | | | | | | |
| C-HPC (19) | | | | | 0.5 | | | |
| C-HPC (20) | | | | | | 0.5 | | |
| Cationized hydroxyethyl cellulose 1 *[1] | | | 0.5 | | | | | |
| Cationized guar gum *[2] | | | | 0.5 | | | | |
| Hydroxypropyl cellulose *[3] | | | | | | | | 0.5 |
| Sodium polyoxyethylene (2) alkylethersulfate *[4] | 7.5 | 7.5 | 7.5 | 7.5 | 7.5 | 7.5 | 7.5 | 7.5 |
| Coconut oil fatty acid amide propyl betaine *[5] | 4.5 | 4.5 | 4.5 | 4.5 | 4.5 | 4.5 | 4.5 | 4.5 |
| Sodium chloride | 1.0 | 1.0 | 1.0 | 1.0 | 1.0 | 1.0 | 1.0 | 1.0 |
| pH Modifier | | | | | q.s. | | | |
| Purified water | | | | | balance | | | |
| pH (diluted 20 times; 25° C.) | 6.0 | 6.0 | 6.0 | 6.0 | 6.0 | 6.0 | 6.0 | 6.0 |
| Evaluation | | | | | | | | |
| Stickiness | 5 | 5 | 4.2 | 4 | 4.4 | 5 | 5 | 2.8 |
| Run fingers through hair | 3.4 | 3.6 | 3 | 3 | 4 | 3.6 | 2.8 | 3 |
| Coating feel | 3.6 | 3.8 | 2.8 | 3 | 3 | 3 | 3.6 | 4 |
| Manageability | 3.4 | 3.8 | 3 | 3 | 3.2 | 3.2 | 3 | 1.8 |

Examples 18 to 47

Production and Evaluation of Shampoos

The respective shampoos having compositions shown in Tables 8 to 10 were produced from the C-HPC (11) and various surfactants and evaluated by the same method as in Example 1. The results are collectively shown in Tables 8 to 10.

TABLE 8

| Hair cosmetic composition (shampoo) | Examples | | | | | | | | | |
|---|---|---|---|---|---|---|---|---|---|---|
| | 18 | 19 | 20 | 21 | 22 | 23 | 24 | 25 | 26 | 27 |
| Formulation (part(s) by mass) | | | | | | | | | | |
| C-HPC (11) | 0.3 | 0.3 | 0.3 | 0.3 | 0.3 | 0.3 | 0.3 | 0.3 | 0.3 | 0.3 |
| Ammonium laurylsulfate | 5.0 | | | | | | | | | |
| Ammonium polyoxyethylene (1) alkylethersulfate *[1] | | 10.0 | | | | | | | | |
| Ammonium polyoxyethylene (3) alkylethersulfate *[2] | 5.0 | | | 3.0 | | | 5.0 | | | 1.0 |
| Sodium polyoxyethylene (1) alkylethersulfate *[3] | | | 10.0 | | | | | | | |
| Sodium alkylsulfate *[4] | | | | 7.0 | | | | | | |
| Sodium polyoxyethylene (4.5) alkyletheracetate *[5] | | | | | 10.0 | | | | | |
| Sodium α-olefin sulfonate *[6] | | | | | | 10.0 | | | | |
| Sodium polyoxyethylene (2) alkylether sulfosuccinate *[7] | | | | | | | 5.0 | | | |
| Sodium acyl glutamate *[8] | | | | | | | | 10.0 | | |
| Alanine derivative *[9] | | | | | | | | | 10.0 | |
| Sodium alkyl benzenesulfonate *[10] | | | | | | | | | | 10.0 |
| Coconut oil fatty acid monoethanol amide | 1.0 | 1.0 | 1.0 | 1.0 | | | | | | |
| Coconut oil fatty acid amide propyl betaine *[11] | | | | | 1.0 | 1.0 | 1.0 | 1.0 | 3.0 | 3.0 | 1.0 |
| pH Modifier | | | | | | | | | q.s. | |

TABLE 8-continued

| Hair cosmetic composition (shampoo) | Examples | | | | | | | | | |
|---|---|---|---|---|---|---|---|---|---|---|
| | 18 | 19 | 20 | 21 | 22 | 23 | 24 | 25 | 26 | 27 |
| Purified water | balance | | | | | | | | | |
| pH (diluted 20 times; 25° C.) | 6.0 | 6.0 | 6.0 | 6.0 | 6.0 | 6.0 | 6.0 | 6.0 | 6.0 | 6.0 |
| Evaluation | | | | | | | | | | |
| Stickiness | 5 | 5 | 5 | 4.8 | 4.8 | 5 | 5 | 4.4 | 4.2 | 5 |
| Run fingers through hair | 4.6 | 4.6 | 4.6 | 4.6 | 4.6 | 4.6 | 4.6 | 4.6 | 4.6 | 4.6 |
| Coating feel | 4.6 | 4.6 | 4.6 | 4.2 | 4.6 | 4.2 | 4.6 | 4.6 | 4.6 | 4.6 |
| Manageability (less dryness) | 4.6 | 4.8 | 4.8 | 4.8 | 4 | 4.2 | 4.8 | 4 | 4 | 4.2 |

Note

[1] "EMAL 170S-A" available from Kao Corp. (effective content: 70%); added in an amount of 14.3%.

[2] "EMAL 327" available from Kao Corp. (effective content: 27%); added in an amount of 18.5%, 11.1% or 3.7%.

[3] "EMAL 170J" available from Kao Corp. (effective content: 70%); added in an amount of 14.3%.

[4] "EMAL O" available from Kao Corp. (effective content: 99%); added in an amount of 7.1%.

[5] "KAOAKYPO RLM-45" available from Kao Corp. (effective content: 92%); added in an amount of 10.9%.

[6] "LIPOLAN LB-440" available from Lion Corp. (effective content: 37%); added in an amount of 27%

[7] "RIKAMILD ES-100" available from New Japan Chemical Co., Ltd. (effective content: 30%); added in an amount of 16.7%.

[8] "AMISOFT LS-11" available from Ajinomoto Co., Inc.

[9] "AMILIGHT ACT-12" available from Ajinomoto Co., Inc. (effective content: 30%); added in an amount of 33.3%.

[10] "NEOPELEX G-25" available from Kao Corp. (effective content: 25%); added in an amount of 40%.

[11] "AMPHITOL 55AB" available from Kao Corp. (effective content: 30%); added in an amount of 3.3% or 10%.

TABLE 9

| Hair cosmetic composition (shampoo) | Examples | | | | | | | | | |
|---|---|---|---|---|---|---|---|---|---|---|
| | 28 | 29 | 30 | 31 | 32 | 33 | 34 | 35 | 36 | 37 |
| Formulation (part(s) by mass) | | | | | | | | | | |
| C-HPC (11) | 0.3 | 0.3 | 0.3 | 0.3 | 0.3 | 0.3 | 0.3 | 0.3 | 0.3 | 0.1 |
| Ammonium polyoxyethylene (1) alkylethersulfate [1] | 10.0 | 10.0 | 10.0 | | 10.0 | 10.0 | | 10.0 | 10.0 | 5.0 |
| Polyoxyethylene (3) lauryl ether | 2.0 | | | | | | | | | |
| Polyoxyethylene (8) lauryl ether | | 2.0 | | | | | | | | |
| Polyoxyethylene (16) cetyl ether | | | 2.0 | | | | | | | |
| Alkyl glycoside [2] | | | | 12.0 | 3.0 | | 3.0 | | | 7.0 |
| Polyoxyethylene (60) hardened castor oil [3] | | | | | | 1.0 | | | | |
| Polyglycerol alkyl ether [4] | | | | | | | 8.0 | | | |
| Polyoxyethylene (6) sorbitan fatty acid ester [5] | | | | | | | | 3.0 | | |
| Coconut oil fatty acid methyl ethanol amide [6] | | | | | | | | | 2.0 | |
| Coconut oil fatty acid monoethanol amide | | | | | | | | | | 0.8 |
| Coconut oil fatty acid amide propyl betaine | | | | 3.0 | | 1.0 | | | | 3.0 |
| pH Modifier | | | | | q.s. | | | | | |
| Purified water | | | | | balance | | | | | |
| pH (diluted 20 times; 25° C.) | 6.0 | 6.0 | 6.0 | 6.0 | 6.0 | 6.0 | 6.0 | 6.0 | 6.0 | 6.0 |
| Evaluation | | | | | | | | | | |
| Stickiness | 5 | 5 | 5 | 5 | 5 | 5 | 5 | 5 | 5 | 5 |
| Run fingers through hair | 4.6 | 4.6 | 4.6 | 4.4 | 4.6 | 4.6 | 4.6 | 4.4 | 4.6 | 4.4 |
| Coating feel | 4.6 | 4.6 | 4.6 | 4.6 | 4.6 | 4.6 | 4.6 | 4.6 | 4.6 | 4.6 |
| Manageability (less dryness) | 4.8 | 4.8 | 5 | 4.2 | 4.6 | 4.8 | 4.2 | 4.8 | 4.8 | 4 |

Note

[1] "EMAL 170S-A" available from Kao Corp. (effective content: 70%); added in an amount of 14.3% or 7.1%.

[2] "MYDOL 10" available from Kao Corp. (effective content: 40%); added in an amount of 30%, 7.5% or 17.5%.

[3] "EMANON CH60" available from Kao Corp.

[4] "SUNSOFT M-12JW" available from Taiyo Kagaku Co., Ltd. (effective content: 60%); added in an amount of 13.3%.

[5] "RHEODOL TW-O106V" available from Kao Corp.

[6] "AMINON C-11S" available from Kao Corp.

TABLE 10

| Hair cosmetic composition (shampoo) | \multicolumn{10}{c}{Examples} | | | | | | | | | |
|---|---|---|---|---|---|---|---|---|---|---|
| | 38 | 39 | 40 | 41 | 42 | 43 | 44 | 45 | 46 | 47 |
| Formulation (part(s) by mass) | | | | | | | | | | |
| C-HPC (11) | 0.3 | 0.3 | 0.3 | 0.3 | 0.3 | 0.3 | 0.3 | 0.3 | 0.3 | 0.1 |
| Cationized guar gum *1 | | | | | | | | | | 0.3 |
| Ammonium polyoxyethylene (1) alkylethersulfate *2 | 10.0 | 10.0 | 10.0 | | 10.0 | 10.0 | 10.0 | 10.0 | 10.0 | 10.0 |
| Sodium polyoxyethylene (2) alkylether sulfosuccinate *3 | | | | 3.0 | | | | | | |
| Lauryl hydroxysulfobetaine *4 | 3.0 | | | | | | | | | 2.0 |
| Lauryl dimethylamineoxide *5 | | 3.0 | | | | | | | | |
| Lauryl carboxymethyl hydroxyimidazolium betaine *6 | | | 3.0 | 8.0 | | | | | | |
| Lauryl dimethyl aminoacetic acid betaine *7 | | | | | 3.0 | | | | | |
| Lauric acid amide propyl betaine *8 | | | | 3.0 | | 3.0 | | | | |
| Cetyl trimethyl ammonium chloride | | | | | | | 0.5 | | | |
| Behenyl trimethyl ammonium chloride | | | | | | | | 0.3 | | |
| Octadecyloxypropyl trimethyl ammonium chloride *9 | | | | | | | | | 0.3 | |
| pH Modifier | | | | | q.s. | | | | | |
| Purified water | | | | | balance | | | | | |
| pH (diluted 20 times; 25° C.) | 6.0 | 6.0 | 6.0 | 6.0 | 6.0 | 6.0 | 6.0 | 6.0 | 6.0 | 6.0 |
| Evaluation | | | | | | | | | | |
| Stickiness | 5 | 5 | 5 | 4.2 | 5 | 5 | 5 | 4.8 | 4.8 | 4.6 |
| Run fingers through hair | 4.6 | 4.6 | 4.6 | 4.6 | 4.6 | 4.8 | 4.6 | 4.6 | 4.6 | 4.4 |
| Coating feel | 4.6 | 4.6 | 4.6 | 4.2 | 4.6 | 4.8 | 4.6 | 5 | 5 | 5 |
| Manageability (less dryness) | 4.8 | 4.8 | 4.8 | 4.2 | 4.4 | 4.8 | 5 | 5 | 5 | 4.8 |

Note
*1 "JAGUAR C-13S" available from Rhodia Corp.
*2 "EMAL 170S-A" available from Kao Corp. (effective content: 70%); added in an amount of 14.3%.
*3 "RIKAMILD ES-100" available from New Japan Chemical Co., Ltd. (effective content: 30%); added in an amount of 10%
*4 "AMPHITOL 20HD" available from Kao Corp. (effective content: 30%); added in an amount of 10% or 6.7%.
*5 "AMPHITOL 20N" available from Kao Corp. (effective content: 35%); added in an amount of 8.6%.
*6 "AMPHITOL 20Y-B" available from Kao Corp. (effective content: 40%); added in an amount of 7.5% or 20%.
*7 "AMPHITOL 20BS" available from Kao Corp. (effective content: 30%); added in an amount of 10%.
*8 "AMPHITOL 20AB" available from Kao Corp. (effective content: 30%); added in an amount of 10%.
*9 "COATAMINE E-80K" available from Kao Corp. (effective content: 45%); added in an amount of 0.67%

From Tables 7 to 10, it was confirmed that the shampoos obtained in Examples 1 to 47 were free from oily sticky feel after drying and therefore could impart good run fingers through hair, coating feel and manageability to hair.

Examples 48 to 59

Production and Evaluation of Conditioners

The respective conditioners having compositions as shown in Table 11 were produced from the C-HPC's (6) and (11) and various surfactants by an ordinary method. More specifically, water and the surfactant except for the polymer were placed in a beaker, heated to 80° C., and then mixed with each other. Then, the polymer solution prepared in the same manner as in Example 1 was added to the resulting solution and uniformly mixed therewith. The obtained mixed solution was mixed with a melted higher alcohol, and the resulting mixture was emulsified while stirring for 30 min, and then cooled. Finally, water was added to the solution to replenish an amount of water evaporated therefrom by heating, and then the pH value of the resulting solution was measured. The pH value of the solution was adjusted with a pH modifier, if required.

The hair bundle was washed with the plain shampoo used in Example 1, and sufficiently wetted with warm water at a temperature of 35 to 40° C. The thus washed hair bundle was applied with 0.5 g of the conditioner having the composition shown in Table 11, rinsed with warm water and wiped with a towel to remove water therefrom, and then set by combing. Thereafter, the hair bundle was dried by a warm air from a dryer and finished by setting with a comb. The thus treated hair bundle was used to evaluate stickiness, run fingers through hair, coating feel and manageability of hair by the same evaluation method according to the same evaluation ratings as used above. The results are shown in Table 11.

Comparative Examples 9 to 11

Production and Evaluation of Conditioners

The respective conditioners having compositions in which the respective components were contained in effective amounts shown in Table 11 were produced from a cationized hydroxyethyl cellulose ("MARCOAT 10" (tradename) available from Nalco Co.), a cationized guar gum ("JAGUAR C-13S" (tradename) available from Rhodia Corp.) and hydroxypropyl cellulose ("CELNY M" (tradename) available from Nippon Soda Co., Ltd.) by the same method as in Example 1, and the conditioners thus produced in Comparative Examples 9 to 11 were evaluated by the same method as used in Examples 48 to 59. The results are collectively shown in Table 11.

TABLE 11

| Hair cosmetic composition (conditioners) | Examples | | | | | | | | | | | | Comparative Examples | | |
|---|---|---|---|---|---|---|---|---|---|---|---|---|---|---|---|
| | 48 | 49 | 50 | 51 | 52 | 53 | 54 | 55 | 56 | 57 | 58 | 59 | 9 | 10 | 11 |
| Formulation (part(s) by mass) | | | | | | | | | | | | | | | |
| C-HPC (6) | 0.3 | | | | | | | | | | | | | | |
| C-HPC (11) | | 0.3 | 0.5 | 0.5 | 0.3 | 0.3 | 0.3 | 0.3 | 0.3 | 0.3 | 0.1 | 0.8 | | | |
| Cationized hydroxyethyl cellulose *1 | | | | | | | | | | | | | 0.3 | | |
| Cationized guar gum *2 | | | 0.2 | | | | | | | | | | | 0.3 | |
| Hydroxypropyl cellulose *3 | | | | | | | | | | | | | | | 0.3 |
| Stearyl trimethyl ammonium chloride | 1.5 | 1.5 | 1.5 | 2.0 | | | 3.0 | | | | 2.0 | 2.0 | 1.5 | 1.5 | 1.5 |
| Octadecyloxypropyl trimethyl ammonium chloride *4 | | | | | 2.0 | | | | | | | | | | |
| Behenyl trimethyl ammonium chloride | | | | | | 1.8 | | | 2.0 | 2.0 | | | | | |
| Behenyl dimethyl amine | | | | | | | 1.8 | | | | | | | | |
| Polyoxyethylene (16) cetyl ether | | | | | | | | | | 0.5 | | | | | |
| Coconut oil fatty acid monoethanol amide | | | | | | | | | | | 0.3 | | | | |
| Stearyl alcohol | 3.0 | 3.0 | 3.0 | 2.5 | 3.0 | 2.0 | 2.2 | | 2.5 | 2.5 | 2.5 | 2.5 | 3.0 | 3.0 | 3.0 |
| Behenyl alcohol | | | | 1.0 | | | | | | | | | | | |
| pH Modifier | | | | | | | | q.s. | | | | | | | |
| Purified water | | | | | | | | balance | | | | | | | |
| pH (diluted 20 times; 25° C.) | 5.5 | 5.5 | 5.0 | 4.5 | 3.5 | 5.5 | 5.5 | 4.5 | 5.5 | 5.5 | 4.5 | 4.5 | 5.5 | 5.5 | 5.5 |
| Evaluation | | | | | | | | | | | | | | | |
| Stickiness | 5 | 5 | 4.6 | 4.8 | 4.8 | 4.8 | 4.6 | 4.6 | 5 | 5 | 5 | 5 | 4 | 3 | 4.2 |
| Run fingers through hair | 4.6 | 4.8 | 4.6 | 4.8 | 5 | 4.8 | 4.6 | 4.4 | 4.4 | 4.6 | 4.4 | 5 | 3 | 3 | 3.2 |
| Coating feel | 4.6 | 5 | 4.8 | 5 | 5 | 5 | 4.8 | 4 | 4.6 | 4.6 | 4.2 | 5 | 3 | 3 | 3.6 |

Note
*1 "MARCOAT 10" available from Nalco Co.
*2 "JAGUAR C-13S" available from Rhodia Corp.
*3 "CELNY M" (tradename) available from Nippon Soda Co., Ltd.
*4 "COATAMINE E-80K" available from Kao Corp. (effective content: 45%); added in an amount of 4.4%

From Table 11, it was confirmed that the conditioners obtained in Examples 48 to 59 were free from oily sticky feel after drying and therefore could impart good run fingers through hair, coating feel and manageability to hair.

Example 60

Hair Shampoo

The hair shampoo having the following composition was produced as follows. That is, purified water, methyl paraben, and the surfactants were placed in a beaker, and heated to 80° C. while stirring. After confirming that the respective components were uniformly dissolved, a C-HPC- and cationic polymer-containing aqueous solution which was previously diluted with water into a concentration of 2% was added to the resulting solution. Then, after cooled to a temperature of 60° C. or lower, silicone was added to the resulting mixed solution, and after cooled to a temperature of 45° C. or lower, a perfume was added thereto, and the resulting mixture was stirred until obtaining a uniform solution. The obtained uniform solution was cooled to room temperature, and water was added to the solution to replenish an amount of water evaporated therefrom by heating, followed by further stirring the solution for 30 min or longer. The thus obtained hair shampoo was evaluated by the same method as in Example 1.

| (Components) | (%) |
|---|---|
| Ammonium polyoxyethylene (1) laurylethersulfate *1 | 12.0 |
| Lauric acid monoethanol amide | 0.8 |
| C-HPC (1) | 0.1 |
| Cationic polymer *2 | 0.1 |

-continued

| (Components) | (%) |
|---|---|
| Silicone *3 | 1.0 |
| Perfume, methyl paraben | q.s. |
| Purified water | balance |
| Total | 100.0 |

Note:
*1 "EMAL 170S-A" available from Kao Corp. (effective content: 70%); added in an amount of 17.1%
*2 "SOFCARE KG101E" available from Kao Corp. (effective content: 40%); added in an amount of 0.25%
*3 "SILICONE BY22-050A" available from Dow Corning Toray Co., Ltd. (effective content: 55%); added in an amount of 1.82%

As a result, it was confirmed that the thus obtained hair shampoo was free from oily sticky feel after drying and therefore exhibited an excellent feeling upon use such as good run fingers through hair, coating feel and manageability.

Example 61

Treatment

The treatment having the following composition was produced as follows. That is, purified water, citric acid, methyl paraben, hydroxyethyl cellulose and dialkyl ($C_{12}$ to $C_{18}$) dimethyl ammonium chloride were placed in a beaker, and heated to 80° C. while stirring, so that the respective components were uniformly dissolved (solution a). Separately, oil components (including cetyl alcohol and stearyl alcohol) and octadecyloxytrimethyl ammonium chloride were placed in another beaker, and the contents of the beaker were heated to 80° C., melted, and uniformly mixed (solution b). The solution b was added to the solution a, and the resulting mixed solution was stirred at 80° C. for 30 min or longer to obtain an emulsion. Then, after the resulting emulsion was cooled to 50° C., the C-HPC (2) and the highly-polymerized dimethyl siloxane (1) were added thereto and uniformly mixed therewith. The obtained mixture was cooled to room temperature, and water was added to the mixture to replenish an amount of water evaporated therefrom by heating, followed by further stirring the mixture for 30 min or longer. The thus obtained treatment was evaluated by the same method as in Example 48.

| (Components) | (%) |
|---|---|
| C-HPC (2) | 0.3 |
| Octadecyloxypropyl trimethyl ammonium chloride [*1] | 2.5 |
| Dialkyl ($C_{12}$ to $C_{18}$) dimethyl ammonium chloride [*2] | 1.0 |
| Cetyl alcohol | 2.5 |
| Stearyl alcohol | 2.5 |
| Highly-polymerized dimethyl siloxane (1) [*3] | 1.0 |
| Hydroxyethyl cellulose [*4] | 0.3 |
| Citric acid | 0.05 |
| Methyl paraben | 0.3 |
| Purified water | balance |
| Total | 100.0 |

Note:
[*1] "COATAMINE E-80K" available from Kao Corp. (effective content: 45%); added in an amount of 5.56%
[*2] "COATAMINE D2345P" available from Kao Corp. (effective content: 75%); added in an amount of 1.33%
[*3] "SILICONE BY22-060" available from Dow Corning Toray Co., Ltd. (effective content: 60%); added in an amount of 1.67%
[*4] "HEC DAICEL SE850" available from Daicel Corp.

As a result, it was confirmed that the thus obtained treatment was free from oily sticky feel after drying and therefore exhibited an excellent feeling upon use such as good run fingers through hair, coating feel and manageability.

Example 62

Hair Styling Agent

The hair styling agent having the following composition was produced as follows. That is, water, stearyl trimethyl ammonium chloride, dipropylene glycol monoethyl ether, behenic acid and methyl paraben were placed in a beaker, and uniformly mixed with each other while being heated to 60° C. An acrylic resin alkanol amine solution was slowly added to the beaker, and after the contents of the beaker were uniformly neutralized, the C-HPC was added thereto. The resulting mixture was cooled to 40° C. or lower, and then ethanol and a perfume were added to the mixture and stirred therewith for 30 min or longer.

The hair bundle was washed with the plain shampoo described in Example 1, and then dried by a warm air from a dryer. The thus dried hair bundle was applied with 0.5 g of the resulting hair styling agent, and then dried by a warm air from a dryer and finished by setting with a comb. The thus treated hair bundle was used to evaluate stickiness, run fingers through hair, coating feel and manageability of hair according to the same evaluation ratings as in Example 1.

| (Components) | (%) |
|---|---|
| C-HPC (3) | 0.8 |
| Stearyl trimethyl ammonium chloride | 2.0 |
| Dipropylene glycol monoethyl ether | 20.0 |
| Behenic acid | 1.5 |
| Acrylic resin alkanol amine solution [*1] | 5.0 |
| Ethanol | 20.0 |
| Perfume, methyl paraben | q.s. |
| Purified water | balance |
| Total | 100.0 |

Note:
[*1] "PLUS-SIZE L-9540B" available from Goo Chemical Co., Ltd. (effective content: 40%); added in an amount of 12.5%

As a result, it was confirmed that the thus obtained hair styling agent was free from oily sticky feel after being finished (dried) and therefore exhibited an excellent feeling upon use such as good run fingers through hair, coating feel and manageability.

Example 63

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.1 |
| Ammonium polyoxyethylene (1) laurylethersulfate [*1] | 15.3 |
| Coconut oil fatty acid monoethanol amide | 1.0 |
| Myristyl alcohol | 0.7 |
| Cationic hydroxyethyl cellulose [*2] | 0.4 |
| Silicone [*3] | 1.4 |
| Ethylene glycol distearate [*4] | 1.0 |
| Perfume, methyl paraben | q.s. |
| Purified water | balance |
| Total | 100.0 |

Note:
[*1] "EMAL 170S-A" available from Kao Corp. (effective content: 70%); added in an amount of 21.9%
[*2] "MARCOAT 10" available from Nalco Co.
[*3] "SILICONE BY22-050A" available from Dow Corning Toray Co., Ltd. (effective content: 55%); added in an amount of 2.5%
[*4] "EUPERLAN PK-810" available from Cognis Corp. (effective content: 20%); added in an amount of 5%

As a result, it was confirmed that the thus obtained hair shampoo was free from oily sticky feel after drying and therefore exhibited an excellent feeling upon use such as good run fingers through hair, coating feel and manageability.

Example 64

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.3 |
| Sodium polyoxyethylene (1) laurylethersulfate [*1] | 12.7 |
| Coconut oil fatty acid amide propyl betaine | 1.4 |
| Coconut oil fatty acid monoethanol amide | 0.6 |
| Cationic guar gum [*2] | 0.3 |

| (Components) | (%) |
|---|---|
| Silicone *3 | 1.7 |
| Ethylene glycol distearate *4 | 1.0 |
| Perfume, sodium benzoate | q.s. |
| Purified water | balance |
| Total | 100.0 |

Note:
*1 "EMAL 170S-A" available from Kao Corp. (effective content: 70%); added in an amount of 18.1%
*2 "JAGUAR C-13S" available from Rhodia Corp.
*3 "SILICONE 1785" available from Dow Corning Toray Co., Ltd. (effective content: 60%); added in an amount of 2.8%
*4 "PEARL CONC. FC-1" available from Kao Corp. (effective content: 20%); added in an amount of 5%

As a result, it was confirmed that the thus obtained hair shampoo was free from oily sticky feel after drying and therefore exhibited an excellent feeling upon use such as good run fingers through hair, coating feel and manageability.

Example 65

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.5 |
| Sodium polyoxyethylene (2) laurylethersulfate *1 | 11.4 |
| Sodium polyoxyethylene (4.5) lauryletheracetate *2 | 3.8 |
| Lauryl dimethyl aminoacetic acid betaine *3 | 1.1 |
| Coconut oil fatty acid monoisopropanol amide | 1.5 |
| Cationic hydroxyethyl cellulose *4 | 0.4 |
| Amino-modified silicone *5 | 0.35 |
| Perfume, methyl paraben | q.s. |
| Purified water | balance |
| Total | 100.0 |

Note:
*1 "EMAL 270S" available from Kao Corp. (effective content: 70%); added in an amount of 16.3%
*2 "KAOAKYPO RLM-45" available from Kao Corp. (effective content: 92%); added in an amount of 4.1%
*3 "AMPHITOL 20BS" available from Kao Corp. (effective content: 30%); added in an amount of 3.8%
*4 "MARCOAT 10" available from Nalco Co.
*5 "SILICONE BY22-079" available from Dow Corning Toray Co., Ltd. (effective content: 14%); added in an amount of 2.5%

As a result, it was confirmed that the thus obtained hair shampoo was free from oily sticky feel after drying and therefore exhibited an excellent feeling upon use such as good run fingers through hair, coating feel and manageability.

Example 66

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.2 |
| Sodium polyoxyethylene (3) laurylethersulfate *1 | 10.5 |
| Coconut oil fatty acid amide propyl betaine *2 | 1.2 |
| Imidazolium betaine *3 | 0.16 |
| Coconut oil fatty acid monoethanol amide | 1.0 |
| Cationic hydroxyethyl cellulose *4 | 0.3 |
| Silicone *5 | 0.83 |
| Ethylene glycol distearate *6 | 1.0 |
| Perfume, sodium benzoate | q.s. |
| Purified water | balance |
| Total | 100.0 |

Note:
*1 "EMAL 327" available from Kao Corp. (effective content: 27%); added in an amount of 38.9%
*2 "AMPHITOL 55AB" available from Kao Corp. (effective content: 30%); added in an amount of 4%
*3 "AMPHITOL 20Y-B" available from Kao Corp. (effective content: 40%); added in an amount of 0.4%
*4 "POIZ C-150L" available from Kao Corp.
*5 "SILICONE BY22-050A" available from Dow Corning Toray Co., Ltd. (effective content: 55%); added in an amount of 1.5%
*6 "EMAL 3201M" available from Kao Corp.

As a result, it was confirmed that the thus obtained hair shampoo was free from oily sticky feel after drying and therefore exhibited an excellent feeling upon use such as good run fingers through hair, coating feel and manageability.

Example 67

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.1 |
| Sodium polyoxyethylene (3) laurylethersulfate *1 | 5.0 |
| Alkyl polyglycoside *2 | 14.0 |
| Coconut oil fatty acid amide propyl betaine | 3.0 |
| Polyoxyethylene-modified silicone *3 | 2.5 |
| Perfume, methyl paraben | q.s. |
| Purified water | balance |
| Total | 100.0 |

Note:
*1 "EMAL 327" available from Kao Corp. (effective content: 27%); added in an amount of 1.85%
*2 "MYDOL 10" available from Kao Corp. (effective content: 40%); added in an amount of 35%
*3 "SILICONE KF-6012" available from Shin-Etsu Chemical Co., Ltd.

As a result, it was confirmed that the thus obtained hair shampoo was free from oily sticky feel after drying and therefore exhibited an excellent feeling upon use such as good run fingers through hair, coating feel and manageability.

Example 68

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.2 |
| Sodium polyoxyethylene (2) laurylethersulfate *1 | 12.0 |
| Sodium polyoxyethylene (10) lauryletheracetate *2 | 4.0 |
| Imidazolium betaine (40%) *3 | 2.4 |
| Coconut oil fatty acid methyl ethanol amide | 2.0 |
| Cationic hydroxyethyl cellulose *4 | 0.5 |
| Perfume, sodium benzoate | q.s. |
| Purified water | balance |
| Total | 100.0 |

Note:
*1 "EMAL 227" available from Kao Corp. (effective content: 27%); added in an amount of 44.4%
*2 "KAOAKYPO RLM-100" available from Kao Corp. (effective content: 89%); added in an amount of 13.3%
*3 "AMPHITOL 20Y-B" available from Kao Corp. (effective content: 40%); added in an amount of 6.0%
*4 "POLYMER LR-30M" available from The Dow Chemical Co.

As a result, it was confirmed that the thus obtained hair shampoo was free from oily sticky feel after drying and therefore exhibited an excellent feeling upon use such as good run fingers through hair, coating feel and manageability.

Example 69

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.3 |
| Lauryl glycoside *1 | 2.4 |
| Polyoxyethylene alkyl ether *2 | 0.8 |
| Coconut oil fatty acid amide propyl betaine *3 | 2.4 |
| 1,2-Hexanediol *4 | 1.0 |
| Cationized hydroxyethyl cellulose *5 | 0.5 |
| Silicone *6 | 1.0 |
| Ethylene glycol distearate (20%) *7 | 0.6 |
| Perfume, sodium benzoate, lactic acid (pH modifier) | q.s. |
| Purified water | balance |
| Total | 100.0 |

Note:
*1 "Plantacare PS10" available from Cognis Corp. (effective content: 40%); added in an amount of 20.0%
*2 "SymMollient W/S 174306" available from Symrise AG
*3 "Dehyton K" available from Cognis Corp. (effective content: 30%); added in an amount of 8.0%
*4 "SymDiol 68" available from Symrise AG
*5 "MARCOAT 10" available from Nalco Co.
*6 "DC190 Surfactant" available from Dow Corning Corp.
*7 "EUPERLAN PK-4000" available from Cognis Corp. (effective content: 20%); added in an amount of 3.0%

As a result, it was confirmed that the thus obtained hair shampoo was free from oily sticky feel after drying and therefore exhibited an excellent feeling upon use such as good run fingers through hair, coating feel and manageability.

Example 70

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.3 |
| Sodium polyoxyethylene laurylethersulfate *1 | 15.7 |
| Coconut oil fatty acid amide propyl betaine *2 | 0.75 |
| Coconut oil fatty acid diethanol amide | 2.0 |
| Cationized guar gum *3 | 0.2 |
| Quaternium-15 *4 | 0.2 |
| Perfume, sodium benzoate, lactic acid (pH modifier) | q.s. |
| Purified water | balance |
| Total | 100.0 |

Note:
*1 "Rhodapex ESY STD" available from Rhodia Corp. (effective content: 70%); added in an amount of 22.4%
*2 "AMPHITOL 55AB" available from Kao Corp. (effective content: 30%); added in an amount of 2.5%
*3 "JAGUAR C-162" available from Rhodia Corp.
*4 "Cosept 200" available from HallStar Co.

As a result, it was confirmed that the thus obtained hair shampoo was free from oily sticky feel after drying and therefore exhibited an excellent feeling upon use such as good run fingers through hair, coating feel and manageability.

Example 71

Hair Shampoo

The hair shampoo having the following composition was produced by the same method as in Example 1, and evaluated according to the same evaluation ratings as in Example 1.

| (Components) | (%) |
|---|---|
| C-HPC (11) | 0.3 |
| Sodium polyoxyethylene (3) laurylethersulfate *1 | 16.1 |
| Coconut oil fatty acid amide propyl betaine *2 | 0.6 |
| Lauric acid monoethanol amide | 3.0 |
| Hydrolyzed protein-modified silicone *3 | 2.0 |
| Perfume, sodium benzoate | q.s. |
| Purified water | balance |
| Total | 100.0 |

Note:
*1 "EMAL 327" available from Kao Corp. (effective content: 27%); added in an amount of 59.6%
*2 "AMPHITOL 55AB" available from Kao Corp. (effective content: 30%); added in an amount of 2.0%
*3 "Pecosil SW-83" available from Phoenix Chemical Inc.

As a result, it was confirmed that the thus obtained hair shampoo was free from oily sticky feel after drying and therefore exhibited an excellent feeling upon use such as good run fingers through hair, coating feel and manageability.

INDUSTRIAL APPLICABILITY

In accordance with the present invention, there is provided a hair cosmetic composition which is free from stickiness when dried after use and is capable of imparting excellent run fingers through hair, coating feel and manageability to hair.

The hair cosmetic composition of the present invention contains a cationized hydroxypropyl cellulose and a surfactant, and can be suitably used in various applications including, for example, hair shampoos, hair rinses, treatments, conditioners, hair creams, blow lotions, hair packs, conditioning gels and conditioning foams.

The invention claimed is:
1. A hair cosmetic composition comprising a surfactant and a cationized hydroxypropyl cellulose, wherein the cationized hydroxypropyl cellulose has a main chain of an anhydroglucose represented by general formula (1) and has a cationized ethyleneoxy group substitution degree of from 0.01 to 2.5 and a propyleneoxy group substitution degree of from 0.1 to 2.8,

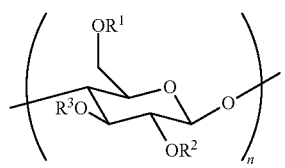

wherein $R^1$, $R^2$ and $R^3$ are each independently a substituent group represented by general formula (2) comprising a cationized ethyleneoxy group and a propyleneoxy group; and n represents an average polymerization degree of the anhydroglucose and is a number of from 50 to 5000, $R^1, R^2, R^3$:

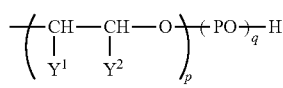

wherein one of $Y^1$ and $Y^2$ is a hydrogen atom and the other of $Y^1$ and $Y^2$ is a cationic group represented by general formula (3); PO is a propyleneoxy group; and p represents a number of cationized ethyleneoxy groups (—CH($Y^1$)—CH($Y^2$)—O—) present in the general formula (2) and q represents a number of propyleneoxy groups (—PO—) present in the general formula (2), and p and q are respectively 0 or a positive number with the proviso that when neither p nor q is 0, the order of addition of the cationized ethyleneoxy group and the propyleneoxy group is not limited, and when neither p nor q is 0 and at least one of p and q are 2 or more, the cationized ethyleneoxy group and the propyleneoxy group may be added by a block bond or a random bond, $Y^1, Y^2$:

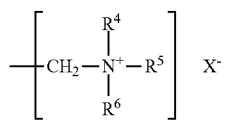

wherein $R^4$, $R^5$ and $R^6$ are each independently a linear or branched alkyl group having 1 to 3 carbon atoms; and $X^-$ is an anionic group.

2. The hair cosmetic composition according to claim 1, wherein a content of the cationized hydroxypropyl cellulose therein is from 0.02 to 10% by mass.

3. The hair cosmetic composition according to claim 1, wherein a mass ratio of the cationized hydroxypropyl cellulose to the surfactant (mass of cationized hydroxypropyl cellulose/mass of surfactant) is in the range of from 0.001 to 10.

4. The hair cosmetic composition according to claim 1, wherein a content of the surfactant therein is from 1 to 50% by mass.

5. The hair cosmetic composition according to claim 1, wherein the surfactant is at least one compound selected from the group consisting of an alkylsulfuric acid salt, a polyoxyethylene alkylethersulfuric acid salt, a polyoxyethylene alkyletheracetic acid salt, a sulfosuccinic acid alkyl ester salt, an acyl glutamic acid salt, a higher fatty acid salt, a polyoxyalkylene alkyl ether, a polyoxyethylene hardened castor oil, a fatty acid alkanol amide, an alkyl glycoside, an alkyl hydroxysulfobetaine, a fatty acid amide propyl betaine, an alkyl dimethyl aminoacitic acid betaine, an alkyl amine oxide, an alkyl trimethyl ammonium salt and an alkyl dimethyl amine salt.

6. The hair cosmetic composition according to claim 1, wherein in the general formula (2), p and q are respectively 0 or 1.

7. The hair cosmetic composition according to claim 1, wherein in the general formula (3), $R^4$, $R^5$ and $R^6$ are each independently a methyl group or an ethyl group.

8. A process for producing a hair cosmetic composition according to claim 1, comprising:
adding a cationizing agent to a pulp and subjecting the resulting mixture to mill treatment to reduce a crystallinity of the pulp, and then adding a base to the obtained mixture and subjecting the mixture to mill treatment to react the pulp with the cationizing agent while further reducing a crystallinity of the pulp, thereby obtaining a cationized cellulose;
reacting the cationized cellulose obtained in said adding with propyleneoxide to obtain a cationized hydroxypropyl cellulose; and
mixing the cationized hydroxypropyl cellulose obtained in said reacting with a surfactant.

9. A method, comprising contacting hair with a hair cosmetic composition according to claim 1, thereby cleansing the hair.

10. The hair cosmetic composition according to claim 1, wherein said cationized hydroxypropyl cellulose has a cationized ethyleneoxy group substitution degree of from 0.08 to 0.6.

11. The hair cosmetic composition according to claim 1, wherein said cationized hydroxypropyl cellulose has a propyleneoxy group substitution degree of from 0.8 to 2.3.

12. The hair cosmetic composition according to claim 1, wherein n is a number of from 350 to 1350.

13. The hair cosmetic composition according to claim 1, wherein a sum of the cationized ethyleneoxy group substitution degree and the propyleneoxy group substitution degree is 3.0 or less.

14. The process for producing a hair cosmetic composition according to claim 8, wherein a mill of said mill treatment is selected from the group consisting of a container-driving media mill and a media-stirring mill.

15. The process for producing a hair cosmetic composition according to claim 8, wherein said base comprises at least one member selected from the group consisting of lithium hydroxide, sodium hydroxide, potassium hydroxide, calcium hydroxide and barium hydroxide.

16. The process for producing a hair cosmetic composition according to claim 8, wherein said base is present, after said adding, in an amount of from 0.05 to 1.0 mol per 1 mol of an anhydroglucose unit present in the cellulose.

17. The process for producing a hair cosmetic composition according to claim 8, wherein said cationizing agent is a glycidyl trialkyl ammonium salt.

18. The process for producing a hair cosmetic composition according to claim 8, wherein said cationizing agent is a glycidyl trialkyl ammonium salt and is added to said pulp in an amount of from 0.01 to 3.0 mol, per 1 mol of an anhydroglucose unit present in the cellulose, during said adding cationizing agent.

19. The process for producing a hair cosmetic composition according to claim 8, wherein said propyleneoxide present during said reacting is present in an amount of from 0.01 to 5.0 mol per 1 mol of an anhydroglucose unit present in a molecule of the cellulose.

20. The hair cosmetic composition according to claim 1, wherein said cationized hydroxypropyl cellulose has a cationized ethyleneoxy group substitution degree of from 0.08 to 0.6 and said cationized hydroxypropyl cellulose has a propyleneoxy group substitution degree of from 0.8 to 2.3.

21. The hair cosmetic composition according to claim 1, wherein said cationized hydroxypropyl cellulose has a cationized ethyleneoxy group substitution degree of from 0.08 to 0.6 and said cationized hydroxypropyl cellulose has a propyleneoxy group substitution degree of from 1.2 to 1.8.

22. The hair cosmetic composition according to claim 1, wherein said cationized hydroxypropyl cellulose has a propyleneoxy group substitution degree of from 1.2 to 1.8.

* * * * *